US011027009B2

(12) United States Patent
Weiner et al.

(10) Patent No.: US 11,027,009 B2
(45) Date of Patent: *Jun. 8, 2021

(54) VACCINES AND IMMUNOTHERAPEUTICS USING IL-28 AND COMPOSITIONS AND METHODS OF USING THE SAME

(71) Applicant: The Trustees of the University of Pennsylvania, Philadelphia, PA (US)

(72) Inventors: David B. Weiner, Merion, PA (US); Matthew Morrow, Bala Cynwyd, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/872,785

(22) Filed: May 12, 2020

(65) Prior Publication Data
US 2020/0268876 A1 Aug. 27, 2020

Related U.S. Application Data

(63) Continuation of application No. 16/127,440, filed on Sep. 11, 2018, now Pat. No. 10,646,563, which is a continuation of application No. 12/936,192, filed as application No. PCT/US2009/039648 on Apr. 6, 2009, now Pat. No. 10,071,154.

(60) Provisional application No. 61/042,674, filed on Apr. 4, 2008.

(51) Int. Cl.
| *C12P 21/02* | (2006.01) |
| *C12N 15/64* | (2006.01) |
| *C07K 14/47* | (2006.01) |
| *C12N 15/24* | (2006.01) |
| *A61K 39/00* | (2006.01) |
| *A61K 39/285* | (2006.01) |
| *C07K 14/54* | (2006.01) |
| *A61K 38/20* | (2006.01) |
| *C12N 7/00* | (2006.01) |

(52) U.S. Cl.
CPC ............ *A61K 39/285* (2013.01); *A61K 38/20* (2013.01); *C07K 14/54* (2013.01); *C12N 7/00* (2013.01); *Y02A 50/30* (2018.01)

(58) Field of Classification Search
CPC ......... A61P 31/12; A61P 31/20; A61P 31/14; A61P 37/08; A61K 38/20
See application file for complete search history.

(56) References Cited

U.S. PATENT DOCUMENTS

| 4,722,848 A | 2/1988 | Paoletti |
| 4,945,050 A | 7/1990 | Sanford |
| 5,017,487 A | 5/1991 | Stunnenberg |
| 5,036,006 A | 7/1991 | Sanford |
| 5,077,044 A | 12/1991 | Stocker |
| 5,110,587 A | 5/1992 | Paoletti |
| 5,112,749 A | 5/1992 | Brey, III |
| 5,174,993 A | 12/1992 | Paoletti |
| 5,223,424 A | 6/1993 | Cochran |
| 5,225,336 A | 7/1993 | Paoletti |
| 5,240,703 A | 8/1993 | Cochran |
| 5,242,829 A | 9/1993 | Panicali |
| 5,273,525 A | 12/1993 | Hofmann |
| 5,294,441 A | 3/1994 | Curtiss, III |
| 5,294,548 A | 3/1994 | McLinden |
| 5,310,668 A | 5/1994 | Ellis |
| 5,387,744 A | 2/1995 | Curtiss, III |
| 5,389,368 A | 2/1995 | Curtiss, III |
| 5,424,065 A | 6/1995 | Curtiss, III |
| 5,439,440 A | 8/1995 | Hofmann |
| 5,451,499 A | 9/1995 | Cochran |
| 5,453,364 A | 9/1995 | Paoletti |
| 5,462,734 A | 10/1995 | Letchworth, III |
| 5,470,734 A | 11/1995 | Sondermeijer |
| 5,482,713 A | 1/1996 | Paoletti |
| 5,580,859 A | 12/1996 | Felgner |
| 5,593,434 A | 1/1997 | Williams |
| 5,593,972 A | 1/1997 | Weiner |
| 5,676,594 A | 10/1997 | Joosten |
| 5,702,359 A | 12/1997 | Hofmann |
| 5,703,055 A | 12/1997 | Felgner |
| 5,739,118 A | 4/1998 | Carrano |
| 5,810,762 A | 9/1998 | Hofmann |
| 5,817,637 A | 10/1998 | Weiner |
| 5,830,876 A | 11/1998 | Weiner |
| 5,962,428 A | 10/1999 | Carrano |
| 5,981,505 A | 11/1999 | Weiner |

(Continued)

FOREIGN PATENT DOCUMENTS

| CN | 1431864 A | 7/2003 |
| CN | 101031316 A | 9/2007 |

(Continued)

OTHER PUBLICATIONS

Li et al., The immunogenicity and protective efficacy of Mtb8.4/hIl-12 chimeric gene vaccine, Vaccine (2006) 24(9):1315-1323.
Gupta et al., Vaccination of Cats with Attenuated Feline Immunodeficiency Virus Proviral DNA Vaccine Expressing Gamma Interferon, Journal of Virology (2007) 81(2):465-473.
Ank Nina et al, 'Lambda interferon (IFN-lambda), a type III IFN, is induced by viruses and IFNs and displays potent antiviral activity against select virus infections in vivo', Journal of Virology, (May 2006), vol. 80, No. 9, ISSN 0022-538X, pp. 4501-4509, XP002694469.

(Continued)

Primary Examiner — Barry A Chestnut
(74) Attorney, Agent, or Firm — Riverside Law LLP

(57) ABSTRACT

Compositions, recombinant vaccines and live attenuated pathogens comprising one or more isolated nucleic acid molecules that encode an immunogen in combination with an isolated nucleic acid molecule that encodes IL-28 or a functional fragment thereof are disclosed. Methods of inducing an immune response in an individual against an immunogen, using such compositions are disclosed.

16 Claims, 14 Drawing Sheets

(56) References Cited

U.S. PATENT DOCUMENTS

| | | | |
|---|---|---|---|
| 6,014,584 | A | 1/2000 | Hofmann |
| 6,055,453 | A | 4/2000 | Hofmann |
| 6,068,650 | A | 5/2000 | Hofmann |
| 6,110,161 | A | 8/2000 | Mathiesen |
| 6,120,493 | A | 9/2000 | Hofmann |
| 6,135,990 | A | 10/2000 | Heller |
| 6,181,964 | B1 | 1/2001 | Hofmann |
| 6,216,034 | B1 | 4/2001 | Hofmann |
| 6,233,482 | B1 | 5/2001 | Hofmann |
| 6,241,701 | B1 | 6/2001 | Hofmann |
| 6,347,247 | B1 | 2/2002 | Dev |
| 6,418,341 | B1 | 7/2002 | Hofmann |
| 6,451,002 | B1 | 9/2002 | Dev |
| 6,516,223 | B2 | 2/2003 | Hofmann |
| 6,567,694 | B2 | 5/2003 | Hayakawa |
| 6,569,149 | B2 | 5/2003 | Dev |
| 6,610,044 | B2 | 8/2003 | Mathiesen |
| 6,654,636 | B1 | 11/2003 | Dev |
| 6,678,556 | B1 | 1/2004 | Nolan |
| 6,697,669 | B2 | 2/2004 | Dev |
| 6,763,264 | B2 | 7/2004 | Hofmann |
| 6,778,853 | B1 | 8/2004 | Heller |
| 6,865,416 | B2 | 3/2005 | Dev |
| 6,927,040 | B2 | 8/2005 | Sheppard |
| 6,939,862 | B2 | 9/2005 | Bureau |
| 6,958,060 | B2 | 10/2005 | Mathiesen |
| 7,038,032 | B2 | 5/2006 | Sheppard |
| 7,135,170 | B2 | 11/2006 | Klucher |
| 7,157,559 | B2 | 1/2007 | Brady |
| 7,245,963 | B2 | 7/2007 | Draghia-Akli |
| 7,351,689 | B2 | 4/2008 | Doyle |
| 7,491,391 | B2 | 2/2009 | Benson |
| 7,786,075 | B2 | 8/2010 | Doyle |
| 2003/0176378 | A1 | 9/2003 | Weiner |
| 2004/0223974 | A1 | 11/2004 | Weiner |
| 2005/0037018 | A1 | 2/2005 | Maertens |
| 2005/0052630 | A1 | 3/2005 | Smith |
| 2006/0165668 | A1 | 7/2006 | Liu |
| 2006/0263368 | A1 | 11/2006 | Rosenblum |
| 2007/0041941 | A1 | 2/2007 | Weiner |
| 2007/0066552 | A1 | 3/2007 | Clarke |
| 2007/0104686 | A1 | 5/2007 | Weiner |
| 2008/0091135 | A1 | 4/2008 | Draghia-Akli |

FOREIGN PATENT DOCUMENTS

| | | |
|---|---|---|
| JP | 2001507216 | 6/2001 |
| JP | 2005525085 | 8/2005 |
| JP | 2007502868 | 2/2007 |
| KR | 20050042458 | 5/2005 |
| WO | 199817799 | 4/1998 |
| WO | 2001087066 | 11/2001 |
| WO | 2003038057 | 5/2003 |
| WO | 2004037995 | 5/2004 |
| WO | 2004112706 A2 | 12/2004 |
| WO | 2005027840 A2 | 3/2005 |
| WO | 2005097165 | 10/2005 |
| WO | 2006012644 A2 | 2/2006 |
| WO | 2009036510 | 3/2009 |

OTHER PUBLICATIONS

M. P. Morrow et al, 'Comparative ability of IL-12 and IL-28B to regulate Treg populations and enhance adaptive cellular immunity', BLOOD, (Mar. 20, 2009), vol. 113, No. 23, doi:10.1182/blood-2008-11-190520, ISSN 0006-4971, pp. 5868-5877, XP055057636.

Lasfar A. et al., "Characterization of the Mouse IFN-A Ligand-Receptor System: IFN-As Exhibit Antitumor Activity against B16 Melanoma", Cancer Research, 2006, 66(8), 4468-4477.

Numasaki M. et al., "IL-28 elicits antitumor responses against murine fibrosarcoma", J Immunol, 2007, 178(8), 5086-5098.

Sato A. et al., "Antitumor activity of IFN-lambda in murine tumor models", J Immunol, 2006, 176(12), 7686-7694.

Bartlett et al., Murine interferon lambdas (type III interferons) exhibit potent antiviral activity in vivo in a poxvirus infection model, 2005, Journal of General Virology, vol. 86, pp. 1589-1596.

Robek M. et al., "Lambda interferon inhibits hepatitis B and C virus replication". J Viral, 2005, 79(6), 3851-3854.

Li M. et al., "Liposome-mediated IL-28 and IL-29 expression in A549 cells and anti-viral effect of IL-28 and IL-29 on WISH cells", Acta Pharmacologica Sinica, 2006, 27(4), 453-459.

Morrow, M.P. et al., 'Cytokines as adjuvants for improving anti-HIV responses', AIDS, 2008, 22:333-338.

Gan et al., Vaccination of mice with recombinant nucleic acid vaccine encoding the intergral membrane protein sf23 and cytokine IL-12 elicits specific immune responses against Schistosoma japonica, National Med. J. China 2005, 85(3): 193-197.

Zhang et al., Construction of eukaryotic expression plasmids encoding IL-18 and study on its immunoenhancement on infectious bursal disease vaccine, Veterinary Immunology (2004) 20(9): 617-621.

Kotenko et al., "IFN-lambdas mediate antiviral protection through a distinct class II cytokine receptor complex", Nat. Immunol., 2003, 4(1):69-77.

Genbank Accession Nos. NP-742150 and AAR24510, 1 page.
Genbank Accession Nos. NP.sub.-742151 and AAR24509, 3 pages.
Genbank Accession No. Q81ZJ0, 1 page.
Genbank Accession No. Q81Z19, 1 page.
Genbank Accession No. NM_173065, 5 pages.
Genbank Accession No. NM_172138, 4 pages.
Genbank Accession No. NM_172139, 3 pages.
Genbank Accession No. AY129153, 1 page.
Genbank Accession No. AY129152, 6 pages.
Genbank Accession No. AY129151, 2 pages.
Genbank Accession No. AY129149, 1 page.
Genbank Accession No. AY129148, 1 page.
Genbank Accession No. AF33540, 4 pages.
Genbank Accession No. AF404757, Jul. 23, 2002, 7 pages.
Genbank Accession No. AF404756, Jul. 23, 2002, 7 pages.
Genbank Accession No. AF404755, Jul. 23, 2002, 7 pages.
Genbank Accession No. AF404754, Jul. 23, 2002, 7 pages.
Genbank Accession No. AF404753, Jul. 23, 2002, 7 pages.
Genbank Accession No. AF481864, May 21, 2002, 7 pages.
Genbank Accession No. M12294, May 8, 2002, 8 pages.
Genbank Accession No. AF317203, Nov. 28, 2008, 7 pages.
GenBank Accession No. AF196835: Lanciotti, R.S. et al., 'West Nile virus strain NY99-flamingo382-99, complete genome,' Dec. 7, 2000.
Genbank Accession No. AF260968, Aug. 27, 2000, 7 pages.
Genbank Accession No. AF260967, Aug. 27, 2000, 7 pages.
GenBank Accession No. AF206518: Anderson, J.F. et al., 'West Nile virus isolate 2741, complete genome,' May 8, 2000, 7 pages.
GenBank Accession No. AF202541: Jia, X.Y. et al., 'West Nile virus strain HNY1999 polyprotein (C, prM, E, NS1, NS2a, NS2b, NS3, NS4a, NS4b, NS5) gene, complete cds,' Dec. 16, 1999, 7 pages.

Howell, M.D. et al., "Limited T-cell receptor beta-chain heterogeneity among interleukin 2 receptor-positive synovial T cells suggests a role for superantigen in rheumatoid arthritis", Proc. Nat. Acad. Sci. USA, 1991, 88:10921-10925.

Williams, W.V. et al., 'Restricted Heterogeneity of T Cell Receptor Transcripts in Rheumatoid Synovium', J. Clin. Invest., 1992, 90, 326-333.

Wucherpfennig, K.W. et al., 'Shared Hyman T Cell Receptor Vp Usage to Immunodominant Regions of Myelin Basic Protein', Science, 1990, 248, 1016-1019.

Oksenberg, J.R. et al., 'Limited heterogeneity of rearranged T-cell receptor Vx transcripts in brains of multiple sclerosis patients', Nature, 1990, 345, 344-346.

Chaudhary, V.K. et al., "A rapid method of cloning functional variable-region antibody genes in Escherichia coli as single-chain immunotoxins," Proc. Nat. Acad. Sci. USA (1990) 87:1066-1070.

Greenland, J.R. et al., "Chemical adjuvants for plasmid DNA vaccines", Vaccine, 2007, 25:3731-3741.

David A. Hokey et al., "DNA vaccines for HIV: challenges and opportunities," Springer Semin Immun, 2006, 28:267-279.

(56) References Cited

OTHER PUBLICATIONS

Schoenly, K.A. et al., "Human immunodeficiency virus type 1 vaccine development: recent advances in the cytotoxic T-lymphocyte platform spotty business", J. Virol., 2008, 82:3166-3180.
Ank, N. et al., "IFN-lambda: novel antiviral cytokines", J Interferon Cytokine Res., 2006, 26:373-379.
Mennechet, F.J. et al., "Interferon-lambda-treated dendritic cells specifically induce proliferation of FOXP3-expressing suppressor T cells", Blood, 2006, 107:4417-4423.
Sheppard et al., "IL-28, IL-29 and their class II cytokine receptor IL-28R", Nat. Immune., 2003, 4(1):63-68.
Uze, G., et al., 'IL-28 and IL-29: newcomers to the interferon family', Biochimie, 2007, 89:729-734.
Siebler, J. et al., "IL-28A is a key regulator of T-cell-mediated liver injury via the T-box transcription factor T-bel.", Gastroenterology, 2007, 132:358-371.
Boyer, J.D. et al., 'SIV DNA vaccine co-administered with IL-12 expression plasmid enhances CD8 SIV cellular immune responses in cynomolgus macaques', J. Med. Primatol., 2005, 34:262-270.
Siew-Yen Chong et al., 'Comparative ability of plasmid IL-12 and IL-15 to enhance cellular and humoral immune responses elicited by a SIV gag plasmid DNA vaccine and alter disease progression following SHIV.sub.89.6P challenge in rhesus macaques,' Vaccine, 2007, 25:4967-4982.
Kim, J.J. et al., "Coadministration of IL-12 or IL-10 expression cassettes drives immune responses toward a Th1 phenotype", J Interferon Cytokine Res, 1998, 18:537-547.
Schadeck, E.B. et al., "A dose sparing effect by plasmid encoded IL-12 adjuvant on a SIV gag-plasmid DNA vaccine in rhesus macaques", Vaccine, 2006, 24:4677-4687.
Sin, J.I. et al., "IL-12 gene as a DNA vaccine adjuvant in a herpes mouse model: IL-12 enhances TH1-type CD4+T cell-mediated protective immunity against herpes simplex virus-2 challenge", J Immunol., 1999, 162:2912-2921.
Hirao, L.A. et al., 'Intradermal subcutaneous immunization by electroporatlon improves plasmid vaccines delivery and potency in pigs and rhesus macaques', Vaccine, 2008, 26(3):440-448.
Laddy et al., 'Heterosubtypic Protection against Pathogenic Human and Avian Influenza Viruses via In Vivo Electroporation of Synthetic Consensus DNA Antigens.', PLOS ONE, (2008), vol. 3, No. 6, pp. E2517-E2518, XP008132555.
Wilson, J.L. et al., "Targeting of human dendritic cells by autologous NK cells", J Immunol., 1999, 163:6365-6370.
DeKruyff, R. H. et al., "Induction of immunoglobulin synthesis by CD4+ T cell clones", Semin Immunol., 1993, 5:421-430.
McFarland, E.J. et al., "In vitro effects of IL-12 on HIV-1-specific CTL lines from HIV-1-infected children", J Immunol., 1998, 161:513-519.
Moore, A. C. et al., "Anti-CD25 antibody enhancement of vaccine-induced immunogenicity: increased durable cellular immunity immunity with reduced immunodominance", J Immunol, 2005, 175:7264-7273.
Tang. Q. et al., "The Foxp3+ regulatory T cell: a jack of all trades, master of regulation", Nat Immunol., 2008, 9:239-244.
Rubio, V. et at., "Ex vivo identification, isolation and analysis of tumor-cytolytic T cells", Nat Med., 2003, 9:1377-1382.
Belyakov, I.M. et al., "Mucosal immunization with HIV-1 peptide vaccine induces mucosal and systemic cytotoxic T lymphocytes and protective immunity in mice against intrarectal recombinant HIV-vaccines challenge", Proc Nail Acad Sci USA, 1998: 95:1709-1714.
Zhao, Z. et al., "IL-12Rbela2 promotes the development of CD4+ CD25+ regulatory T cells", J Immunol., 2008, 181:3870-3876.
Notice of Allowance dated May 11, 2018 for U.S. Appl. No. 12/936,192 (pp. 1-7).
Gustafsson et al. Codon bias and heterologous protein expression. Trends in Biotech. 2004; 22(7):346-353.
Dos Reis et al. Solving the riddle of codon usage preferences: a test for translational selection. Nucleic Acids Res. 2004; 32(17): 5036-5044.
Wang et al. Relative contributions of codon usage, promoter efficiency and leader sequence to the antigen expression and immunogenicity of HIV-1 ENV DNA vaccine. Vaccine, 2006; 24: 4531-4540).
Rolland et al., 'Reconstruction and function of ancestral center-of-tree human immunodeficiency virus type 1 proteins,' J. Virol., 2007, 81(16):8507-14.
Chinese Office Action (with English language translation) for Appl. No. 201511000252.5, dated Mar. 25, 2019, 42 pages.
Chinese Office Action (with English language translation) for Appl. No. 201511000252.5, dated Jun. 5, 2018, 37 pages.
Translation of Chinese Search Report for Appl. No. 201511000252.5, dated May 28, 2018, 2 pages.
Yang Yeh-hua, Molecular Biology of Genes, Higher Education Press, Jan. 31, 2008, p. 182.—cited in CN OA (201511000252.5) dtd Mar. 25, 2019.
"Biotechnology Pharmacy", Wu Wutong ed., Higher Educatin Press, 1st Edition, Sep. 2003, p. 252.—cited in CN OA (201511000252.5) dtd Mar. 25, 2019.
Dou Jun et al., "Vaccine Engineering", Southeast University Press, Oct. 30, 2007, pp. 375-376.—cited in CN OA (201511000252.5) dtd Mar. 25, 2019.
Office Action dated Apr. 1, 2019 for U.S. Appl. No. 16/127,440 (pp. 1-5).
Office Action dated Sep. 25, 2019 for U.S. Appl. No. 16/127,440 (pp. 1-8).
Notice of Allowance dated Jan. 8, 2020 for U.S. Appl. No. 16/127,440 (7 pages).
Kim et al., "In Vivo Engineering of a Cellular Immune Response by Coadministration of IL-12 Expression Vector with a DNA Immunogen" 1997, Journal of Immunology, 158:816-826.
Pillard et al., "Evidence for the Effects of a Superantigen in Rheumatoid Arthritis" 1991, Science, 253, 325-329.

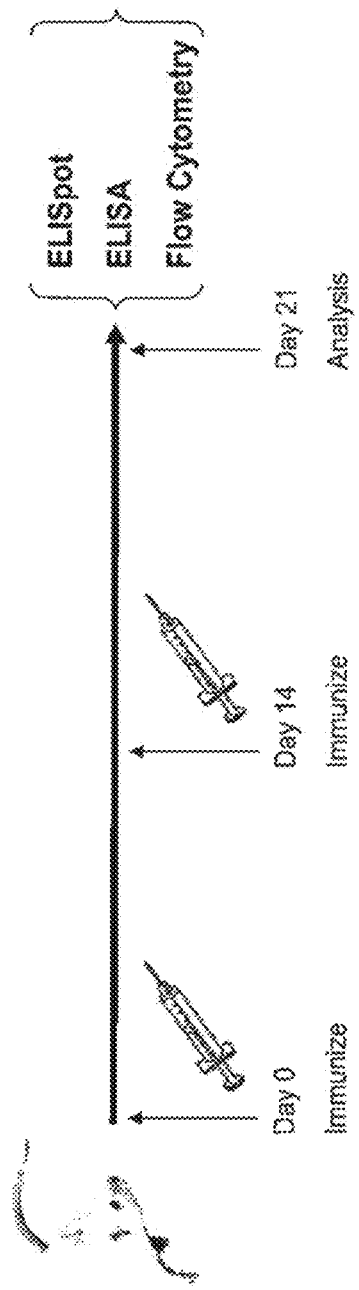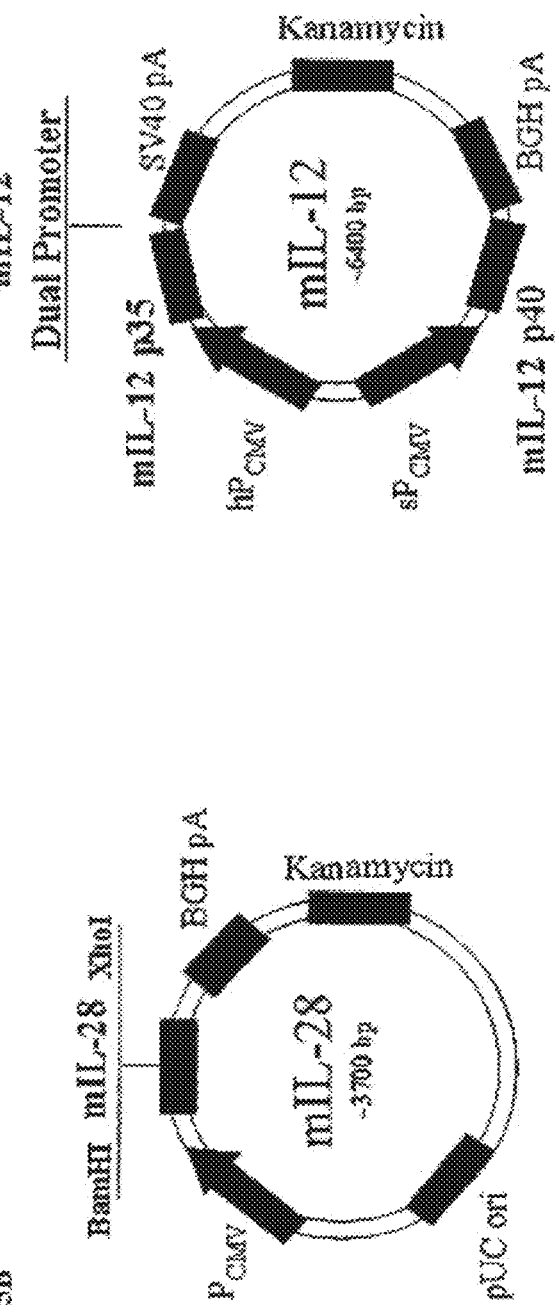
Figure 5A
Figure 5B

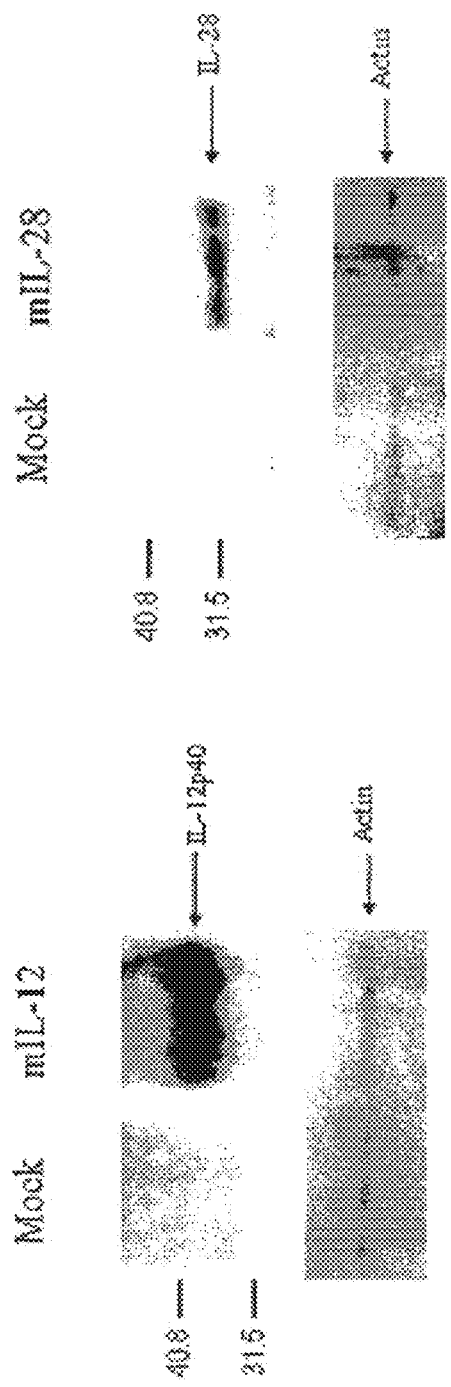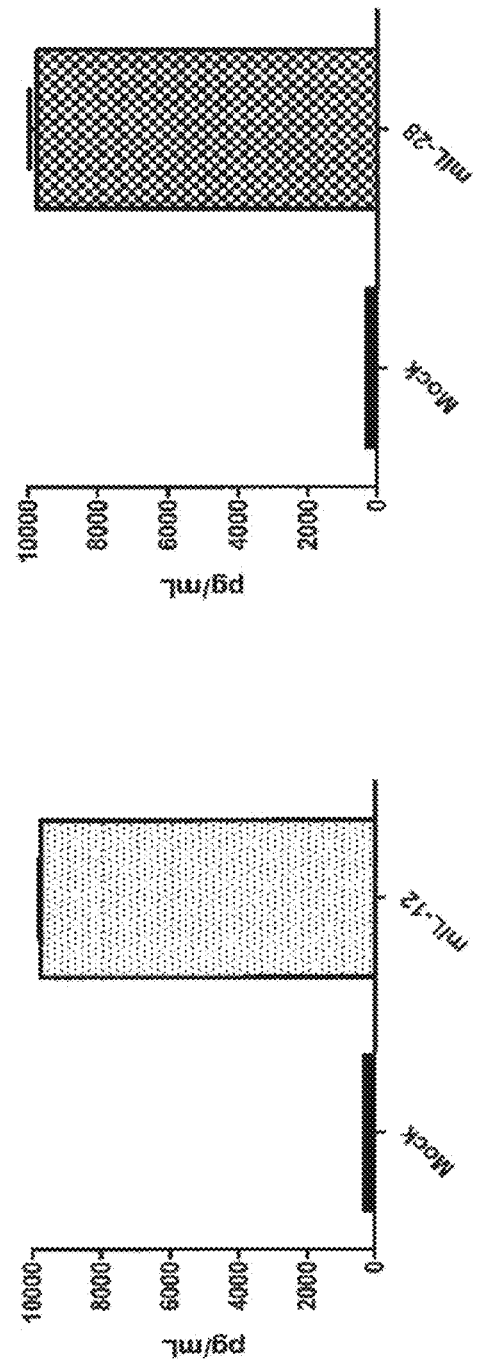
Figure 6A
Figure 6B

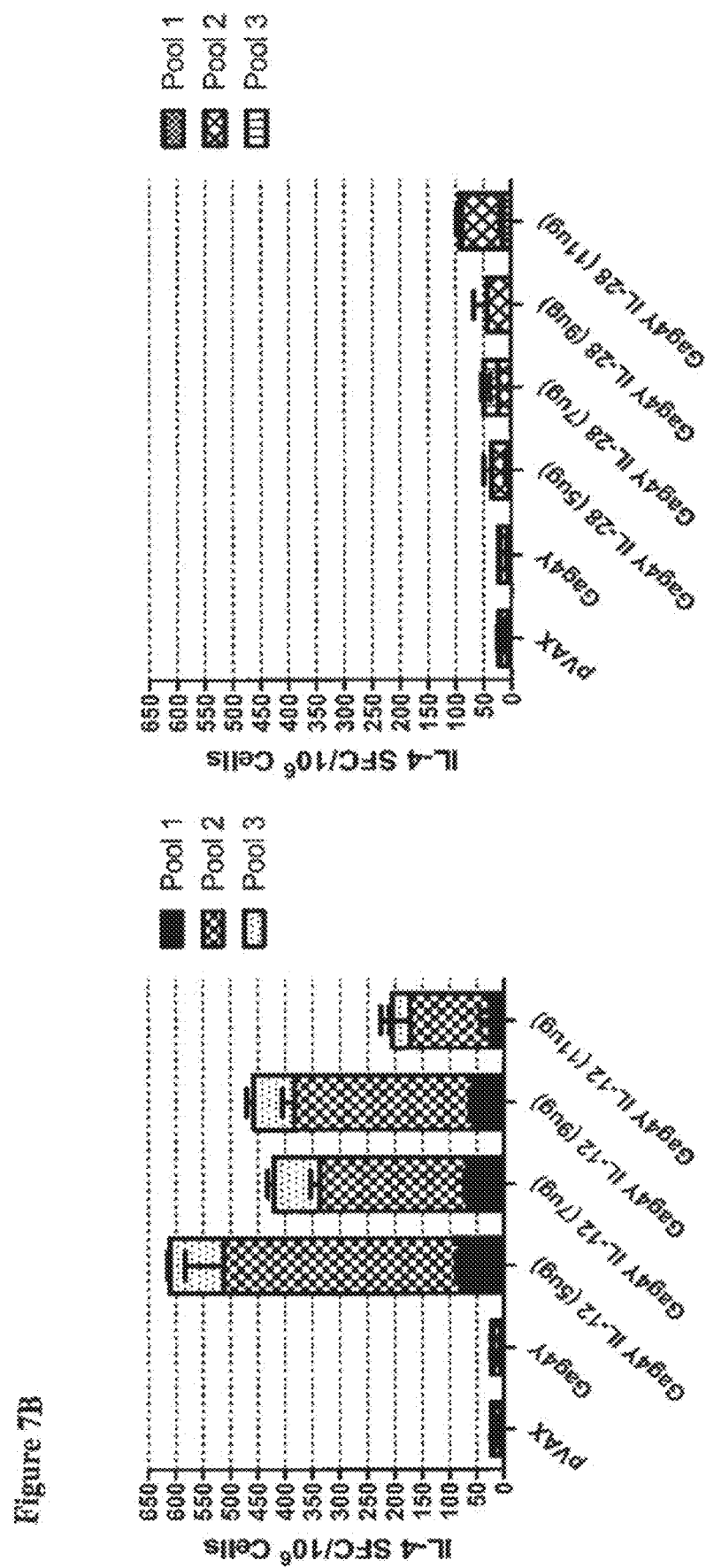

VACCINES AND IMMUNOTHERAPEUTICS USING IL-28 AND COMPOSITIONS AND METHODS OF USING THE SAME

This application claims priority to U.S. Provisional Application No. 61/042,674 filed Apr. 4, 2008, which is incorporated herein by reference.

CROSS-REFERENCE TO RELATED APPLICATIONS

This application is a Continuation of U.S. application Ser. No. 16/127,440, filed Sep. 11, 2018, which is a Continuation of U.S. application Ser. No. 12/936,192, filed Jan. 11, 2011 claiming benefit to International Patent Application No. PCT/US2009/039648, filed on Apr. 6, 2009, which is entitled to priority under 35 U.S.C. § 119(e) to U.S. Provisional Application Ser. No. 61/042,674, filed Apr. 4, 2008, the disclosures of which are incorporated herein by reference in their entireties.

FIELD OF THE INVENTION

The present invention relates to improved vaccines, improved methods for prophylactically and/or therapeutically immunizing individuals against immunogens, and to improved immunotherapeutic compositions and improved immunotherapy methods.

BACKGROUND OF THE INVENTION

Immunotherapy refers to modulating a person's immune responses to impart a desirable therapeutic effect. Immunotherapeutics refer to those compositions which, when administered to an individual, modulate the individual's immune system sufficient to ultimately decrease symptoms which are associated with undesirable immune responses or to ultimately alleviate symptoms by increasing desirable immune responses. In some cases, immunotherapy is part of a vaccination protocol in which the individual is administered a vaccine that exposes the individual to an immunogen against which the individual generates an immune response in such cases, the immunotherapeutic increases the immune response and/or selectively enhances a portion of the immune response (such as the cellular arm or the humoral arm) which is desirable to treat or prevent the particular condition, infection or disease.

U.S. Pat. No. 7,135,170, which is incorporated herein by reference, discloses nucleic acid and amino acid sequences of human IL-28A and human IL-28B and the administration of IL-28A or IL-28B protein to individuals infected with a virus.

U.S. Pat. No. 7,491,391, which is incorporated herein by reference, discloses antibodies that bind to IL-23p19. Compositions comprising the antibodies and uses comprising administration of the antibodies in combination with other agents are described including the anti-IL-23p19 antibody in combination with any interleukin protein includes IL-28.

U.S. Patent Application Publication No. 20050037018, which is incorporated herein by reference, discloses HCV vaccines in combination with antiviral agents to treat individuals who are infected with HCV. IL-28 protein is included in the list of antiviral compounds used to treat HCV-infected individuals in combination with the HCV vaccines disclosed.

U.S. Patent Application Publication No. 20060165668, which is incorporated herein by reference, discloses cancer cells transfected with nucleic acid molecules encoding two or more therapeutic proteins, and treating individuals who have cancer by administering such cancer cells to them. Cytokines are included among the therapeutic proteins listed and IL-28 is included in the list of cytokines.

U.S. Patent Application Publication No. 20060263368, which is incorporated herein by reference, discloses anti-cancer compounds which includes a cancer cell targeting moiety and a anti-cell proliferation moiety and the use of such compounds to treat cancer and prevent or reverse chemoresistance of cancer cells. Hormones are included among the cancer cell targeting moiety listed and IL-28 is included in the list of hormones.

U.S. Patent Application Publication No. 20070066552, which is incorporated herein by reference, discloses formulations for delivering nucleic acid molecules that encode therapeutic proteins. IL-28 is included among the list of proteins described as therapeutic proteins.

Vaccine protocols can be improved by the delivery of agents that modulate a person's immune responses to induce an improved immune response. In some vaccination protocols in which the individual is administered a vaccine that exposes the individual to an immunogen against which the individual generates an immune response, an agent is provided that increases the immune response and/or selectively enhances a portion of the immune response (such as the cellular arm or the humoral arm) which is desirable to treat or prevent the particular condition, infection or disease.

Vaccines are useful to immunize individuals against target antigens such as allergens, pathogen antigens or antigens associated with cells involved in human diseases. Antigens associated with cells involved in human diseases include cancer-associated tumor antigens and antigens associated with cells involved in autoimmune diseases.

In designing such vaccines, it has been recognized that vaccines that produce the target antigen in cells of the vaccinated individual are effective in inducing the cellular arm of the immune system. Specifically, live attenuated vaccines, recombinant vaccines which use avirulent vectors and DNA vaccines each lead to the production of antigens in the cell of the vaccinated individual which results in induction of the cellular arm of the immune system. On the other hand, killed or inactivated vaccines, and sub-unit vaccines which comprise only proteins do not induce good cellular immune responses although they do induce an effective humoral response.

A cellular immune response is often necessary to provide protection against pathogen infection and to provide effective immune-mediated therapy for treatment of pathogen infection, cancer or autoimmune diseases. Accordingly, vaccines that produce the target antigen in cells of the vaccinated individual such as live attenuated vaccines, recombinant vaccines that use avirulent vectors and DNA vaccines are often preferred.

While such vaccines are often effective to immunize individuals prophylactically or therapeutically against pathogen infection or human diseases, there is a need for improved vaccines. There is a need for compositions and methods that produce an enhanced immune response.

Likewise, while some immunotherapeutics are useful to modulate immune response in a patient there remains a need for improved immunotherapeutic compositions and methods.

SUMMARY OF THE INVENTION

The present invention relates to a composition an isolated nucleic acid molecule that encodes an immunogen in combination with an isolated nucleic acid molecule that encodes or IL-28 or functional fragments thereof.

The present invention further relates to a composition an isolated nucleic acid molecule that encodes both an immunogen and IL-28 or functional fragments thereof.

The present invention relates to injectable pharmaceutical compositions comprising an isolated nucleic acid molecule that encodes an immunogen in combination with an isolated nucleic acid molecule that encodes IL-28 or functional fragments thereof.

The present invention relates to injectable pharmaceutical compositions comprising an isolated nucleic acid molecule that encodes both an immunogen and IL-28 or functional fragments thereof.

The present invention further relates to methods of inducing an immune response in an individual against an immunogen, comprising administering to the individual a composition an isolated nucleic acid molecule that encodes an immunogen in combination with an isolated nucleic acid molecule that encodes IL-28 or functional fragments thereof.

The present invention further relates to methods of inducing an immune response in an individual against an immunogen, comprising administering to the individual a nucleic acid molecule that encodes an immunogen and IL-28 or functional fragments thereof.

The present invention further relates to recombinant vaccines comprising a nucleotide sequence that encodes an immunogen operably linked to regulatory elements, a nucleotide sequences that encode IL-28 or functional fragments thereof, and to methods of inducing an immune response in an individual against an immunogen comprising administering such a recombinant vaccine to an individual.

The present invention further relates to a live attenuated pathogen, comprising a nucleotide sequence that encodes IL-28 or functional fragments thereof, and to methods of inducing an immune response in an individual against a pathogen comprising administering the live attenuated pathogen to an individual.

BRIEF DESCRIPTION OF THE FIGURES

FIGS. 5A and 5B show immunization schedules and plasmid maps. FIG. 5A indicates that mice were immunized on Day 0 and Day 14 with a multi-clade HIV Gag construct and with or without adjuvant, followed by electroporation using the CELLECTRA® adaptive constant current device after each immunization. On Day 21 mice were sacrificed and lymphocytes were isolated and analyzed. FIG. 5B shows plasmid maps for murine IL-28B and IL-12 constructs.

FIGS. 6A and 6B show expression and secretion of murine IL-12 and murine IL-28B in vitro. FIG. 6A shows data from Western blotting for murine IL-12p40 and murine IL-28 proteins from HEK 293T cell lysates 48 hours post transfection. Mock transfected cells received empty pVAX vector. FIG. 6B shows data from ELISAs which show secretion of the active IL-12 p35/p40 heterodimer as well as the IL-28 protein into the supernatants of transfected cells.

FIGS. 7A and 7B show HIV Gag Specific IFNγ and IL-4 ELISpots from Isolated Splenocytes. FIG. 7A shows the effects of cytokine adjuvants on the induction of a Th1 response measured via the use antigen-specific IFNγ ELISpots performed on isolated splenocytes. ELISpots were performed on splenocytes harvested from mice that received IL-12 as an adjuvant or IL-28B as an adjuvant (n=4) and IFNγ spot forming units (SFU) were counted. FIG. 7B shows the effects of cytokine adjuvants on the induction of a Th2 response measured in the same fashion using IL-4 ELISpots.

(FIG. 8A shows total IgG. FIG. 8B shows IgG1. FIG. 8C shows IgG2a.

FIG. 11A shows the effects of IL-12 and IL-28 on the induction of a Th1 response measured via the use antigen-specific IFNγ ELISpots performed on isolated splenocytes. FIG. 11B shows data from experiments in which mice (n=8) were immunized on Day 0 and Day 14 with the influenza NP construct and with or without adjuvant, followed by electroporation using the CELLECTRA® adaptive constant current device after each immunization. On Day 42, mice were challenge intranasally with 10 LD50 of A/PR/8/34, an H1N1 influenza strain. Mortality associated with influenza infection was tracked over the course of 14 days (FIG. 11B).

DETAILED DESCRIPTION OF PREFERRED EMBODIMENTS

Figure 1:
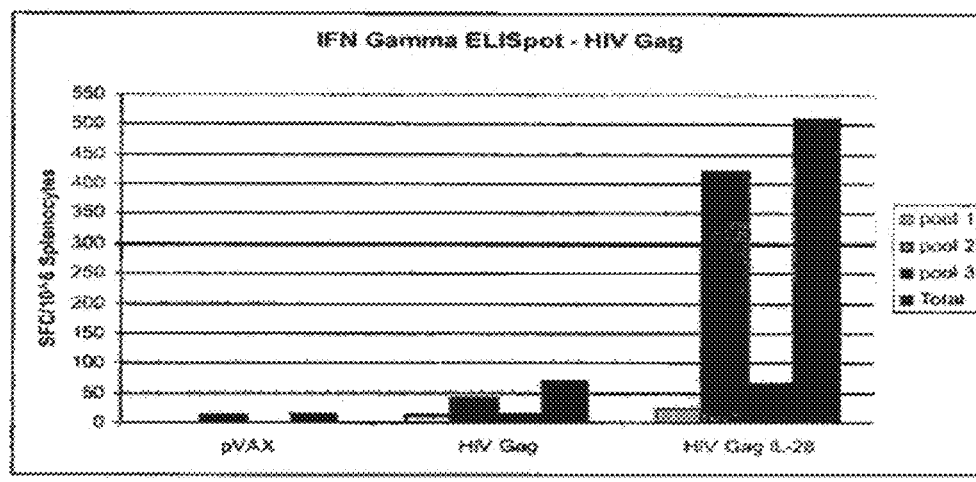
FIG. 1 shows data from experiments measuring interferon gamma response from mouse splenocytes when compared with mice that were immunized with the Gag plasmid in the presence or absence of IL-28 co-treatment.

As used herein, the term "IL-28" refers to interleukin 28 protein, which is an interferon lambda, including different variants thereof, such as, but not limited to, IL-28A, IL-28B and IL-28C.

As used herein, "functional fragment" is meant to refer to a fragment of IL-28 that, when delivered in conjunction with an immunogen, provides an increased immune response compared to the immune that is induced when the immunogen is delivered without the fragment. Fragments are generally 10 or more amino acids in length.

As used herein the term "target protein" is meant to refer to peptides and protein encoded by gene constructs of the present invention that act as target proteins for an immune response. The terms "target protein" and "immunogen" are used interchangeably and refer to a protein against which an immune response can be elicited. The target protein is an immunogenic protein that shares at least an epitope with a protein from the pathogen or undesirable cell-type such as a cancer cell or a cell involved in autoimmune disease against which an immune response is desired. The immune response directed against the target protein will protect the individual against and/or treat the individual for the specific infection or disease with which the target protein is associated. In some embodiments, the target protein is a pathogen antigen such as a viral protein or fragment thereof. In some embodiments, the target protein is a viral protein or fragment thereof from HCV. In some embodiments, the target protein is a viral protein or fragment thereof from a virus other than HCV.

As used herein, the term "genetic construct" refers to the DNA or RNA molecules that comprise a nucleotide sequence which encodes a target protein or immunomodulating protein. The coding sequence includes initiation and termination signals operably linked to regulatory elements including a promoter and polyadenylation signal capable of directing expression in the cells of the individual to whom the nucleic acid molecule is administered.

As used herein, the term "expressible form" refers to gene constructs that contain the necessary regulatory elements operably linked to a coding sequence that encodes a target protein or an immunomodulating protein, such that when present in the cell of the individual, the coding sequence will be expressed.

As used herein, the term "sharing an epitope" refers to proteins that comprise at least one epitope that is identical to or substantially similar to an epitope of another protein.

As used herein, the term "substantially similar epitope" is meant to refer to an epitope that has a structure that is not identical to an epitope of a protein but nonetheless invokes a cellular or humoral immune response that cross-reacts to that protein.

As used herein, the term "intracellular pathogen" is meant to refer to a virus or pathogenic organism that, at least part of its reproductive or life cycle, exists within a host cell and therein produces or causes to be produced, pathogen proteins.

As used herein, the term "hyperproliferative diseases" is meant to refer to those diseases and disorders characterized by hyperproliferation of cells.

As used herein, the term "hyperproliferative-associated protein" is meant to refer to proteins that are associated with a hyperproliferative disease.

The invention arises from the discovery that when delivered as part of a vaccine, nucleic acid molecules that encode IL-28 and functional fragments thereof, and combinations thereof modulate immune responses. Accordingly nucleic acid molecules that encode IL-28 and functional fragments thereof, and combinations thereof may be delivered as immunotherapeutics in combination with or as components of a vaccine.

IL-28 proteins and nucleic acid molecules that encode such proteins are disclosed in U.S. Pat. Nos. 7,135,170 and 7,157,559, which are each incorporated herein by reference. In addition, U.S. Pat. Nos. 6,927,040 and 7,038,032 are each incorporated herein by reference. Interferon-like protein Zcyto21, Kotenko et al., Nat. Immunol. 4(1):69-77, 2003 and Sheppard et al., Nat. Immunol. 4(1):63-68, 2003, are also incorporated herein by reference GENBANK Accession numbers for the protein sequence for human IL-28A are NP 742150 and AAR24510, which are each incorporated herein by reference.

GENBANK Accession numbers for the protein sequence for human IL-28B are NP 742151 and AAR24509, which are each incorporated herein by reference.

GENBANK Accession number for the protein sequence for human IL-28C is AAQ01561, which is incorporated herein by reference.

GENBANK Accession number Q8IZJO, which is incorporated herein by reference, refers to Interleukin-28A precursor (IL-28A) (Interferon lambda-2) (IFN-lambda-2) (Cytokine ZCYTO20).

GENBANK Accession number Q8IZ19, which is incorporated herein by reference, refers to Interleukin-28B precursor (IL-28B) (IL-28C) (Interferon lambda-3) (IFN-lambda-3) (Interferon lambda-4) (IFN-lambda-4) (Cytokine ZCYTO22).

GENBANK Accession number NM_173065, which is incorporated herein by reference, refers to *Homo sapiens* interleukin 28 receptor, alpha (interferon, lambda receptor) (IL28RA), transcript variant 3, mRNA.

GENBANK Accession number NM_172138, which is incorporated herein by reference, refers to *Homo sapiens* interleukin 28A (interferon, lambda 2) (IL28A), mRNA.

GENBANK Accession number NM_172139, which is incorporated herein by reference, refers to *Homo sapiens* interleukin 28B (interferon, lambda 3) (IL28B), mRNA.

GENBANK Accession number AY129153, which is incorporated herein by reference, refers to *Homo sapiens* interleukin 28 receptor A splice variant 3 (IL28RA) mRNA, complete cds; alternatively spliced.

GENBANK Accession number AY129152, which is incorporated herein by reference, refers to *Homo sapiens* interleukin 28 receptor A splice variant 2 (IL28RA) mRNA, complete cds; alternatively spliced.

GENBANK Accession number AY129151, which is incorporated herein by reference, refers to *Homo sapiens* interleukin 28 receptor A (IL28RA) mRNA, complete cds; alternatively spliced GENBANK Accession number AY129149, which is incorporated herein by reference, refers to *Homo sapiens* interleukin 28B (IL28B) mRNA, complete cds.

GENBANK Accession number AY129148, which is incorporated herein by reference, refers to *Homo sapiens* interleukin 28A (IL28A) mRNA, complete cds.

According to some embodiments of the invention, the delivery of a nucleic acid sequence that encodes IL-28 or functional fragments thereof, and combination with a nucleic acid sequence that encodes an immunogen to an individual enhances the immune response against the immunogen. When the nucleic acid molecules that encode the transcription factors are taken up by cells of the individual the nucleotide sequences that encode the IL-28 or functional fragments thereof, and the immunogen are expressed in the cells, the proteins are thereby delivered to the individual. Aspects of the invention provide methods of delivering the coding sequences of the proteins on a single nucleic acid molecule, methods of delivering the coding sequences of the proteins on different nucleic acid molecules and methods of delivering the coding sequences of the proteins as part of recombinant vaccines and as part of attenuated vaccines.

According to some aspects of the present invention, compositions and methods are provided which prophylactically and/or therapeutically immunize an individual against a pathogen or abnormal, disease-related cells. The vaccine may be any type of vaccine such as, a live attenuated vaccine, a recombinant vaccine or a nucleic acid or DNA vaccine. By delivering nucleic acid molecules that encode an immunogen and IL-28 or functional fragments thereof the immune response induced by the vaccine may be modulated. IL-28 is particularly useful when delivered via an expressible nucleic acid molecule, such as for example as part of a plasmid or the genome of a recombinant vector or attenuated pathogen or cell. IL-28 is particularly useful when delivered prophylactically in order to induce a protective immune response in an uninfected or disease free individual. IL-28B is particularly useful form of IL-28. IL-28 is particularly useful when delivered to induce a protective immune response in humans. In some embodiments, nucleic acid molecules encoding IL-28 are delivered in a cell free composition. In some embodiments, nucleic acid molecules encoding IL-28 are delivered in a composition free of cancer cells. In some embodiments, IL-28 or nucleic acid molecules encoding IL-28 are administered free of any other cytokine. In some embodiments, IL-28 or nucleic acid molecules encoding IL-28 are provided without non-IL-28 sequences incorporated therein or linked thereto.

Isolated cDNA that encodes the immunomodulating proteins are useful as a starting material in the construction of constructs that can produce that immunomodulating protein. Using standard techniques and readily available starting materials, a nucleic acid molecule that encodes an immunomodulating protein may be prepared.

The present invention relates to compositions for delivering the immunomodulating proteins and methods of using the same. Aspects of the present invention relate to nucleic acid molecules that comprise a nucleotide sequence that encodes IL-28 or functional fragments thereof operably linked to regulatory elements in combination with a nucleotide sequence that encodes an immunogen operably linked to regulatory elements Aspects of the present invention relate to compositions which comprise a nucleic acid molecule that comprises a nucleotide sequence that encodes IL-28 or functional fragments thereof operably linked to regulatory elements in combination with a nucleic acid molecule that comprises a nucleotide sequence that encodes an immunogen operably linked to regulatory elements. The present invention further relates to injectable pharmaceutical compositions that comprise such nucleic acid molecules.

The nucleic acid molecules may be delivered using any of several well known technologies including DNA injection (also referred to as DNA vaccination), recombinant vectors such as recombinant adenovirus, recombinant adenovirus associated virus and recombinant vaccinia virus.

DNA vaccines are described in U.S. Pat. Nos. 5,593,972, 5,739,118, 5,817,637, 5,830,876, 5,962,428, 5,981,505, 5,580,859, 5,703,055, 5,676,594, and the priority applications cited therein, which are each incorporated herein by reference. In addition to the delivery protocols described in those applications, alternative methods of delivering DNA are described in U.S. Pat. Nos. 4,945,050 and 5,036,006, which are both incorporated herein by reference.

Routes of administration include, but are not limited to, intramuscular, intranasally, intraperitoneal, intradermal, subcutaneous, intravenous, intraarterially, intraoccularly and oral as well as topically, transdermally, by inhalation or suppository or to mucosal tissue such as by lavage to vaginal, rectal, urethral, buccal and sublingual tissue. Preferred routes of administration include to mucosal tissue, intramuscular, intraperitoneal, intradermal and subcutaneous injection. Genetic constructs may be administered by means including, but not limited to, traditional syringes, needleless injection devices, or "microprojectile bombardment gene guns".

Another route of administration involves the use of electroporation to deliver the genetic construct, as described in U.S. Pat. Nos. 5,273,525, 5,439,440, 5,702,359, 5,810,762, 5,993,434, 6,014,584, 6,055,453, 6,068,650, 6,110,161, 6,120,493, 6,135,990, 6,181,964, 6,216,034, 6,233,482, 6,241,701, 6,347,247, 6,418,341, 6,451,002, 6,516,223, 6,567,694, 6,569,149, 6,610,044, 6,654,636, 6,678,556, 6,697,669, 6,763,264, 6,778,853, 6,865,416, 6,939,862 and 6,958,060, which are hereby incorporated by reference.

Examples of electroporation devices and electroporation methods preferred for facilitating delivery of the DNA vaccines include those described in U.S. Pat. No. 7,245,963 by Draghia-Akli, et al., U.S. Patent Pub. 2005/0052630 submitted by Smith, et al., the contents of which are hereby incorporated by reference in their entirety. Also preferred, are electroporation devices and electroporation methods for facilitating delivery of the DNA vaccines provided in co-pending and co-owned U.S. patent application Ser. No. 11/874,072, filed Oct. 17, 2007, which claims the benefit under 35 USC 119(e) to U.S. Provisional Applications Ser. Nos. 60/852,149, filed Oct. 17, 2006, and 60/978,982, filed Oct. 10, 2007, all of which are hereby incorporated in their entirety.

The following is an example of an embodiment using electroporation technology, and is discussed in more detail in the patent references discussed above: electroporation devices can be configured to deliver to a desired tissue of a mammal a pulse of energy producing a constant current similar to a preset current input by a user. The electroporation device comprises an electroporation component and an electrode assembly or handle assembly. The electroporation component can include and incorporate one or more of the various elements of the electroporation devices, including: controller, current waveform generator, impedance tester, waveform logger, input element, status reporting element, communication port, memory component, power source, and power switch. The electroporation component can function as one element of the electroporation devices, and the other elements are separate elements (or components) in communication with the electroporation component. In some embodiments, the electroporation component can function as more than one element of the electroporation devices, which can be in communication with still other elements of the electroporation devices separate from the electroporation component. The use of electroporation technology to deliver the CD28 constructs is not limited by the elements of the electroporation devices existing as parts of one electromechanical or mechanical device, as the elements can function as one device or as separate elements in communication with one another. The electroporation component is capable of delivering the pulse of energy that produces the constant current in the desired tissue, and includes a feedback mechanism. The electrode assembly includes an electrode array having a plurality of electrodes in a spatial arrangement, wherein the electrode assembly receives the pulse of energy from the electroporation component and delivers same to the desired tissue through the electrodes. At least one of the plurality of electrodes is neutral during delivery of the pulse of energy and measures impedance in the desired tissue and communicates the impedance to the electroporation component. The feedback mechanism can receive the measured impedance and can adjust the pulse of energy delivered by the electroporation component to maintain the constant current.

In some embodiments, the plurality of electrodes can deliver the pulse of energy in a decentralized pattern. In some embodiments, the plurality of electrodes can deliver the pulse of energy in the decentralized pattern through the control of the electrodes under a programmed sequence, and the programmed sequence is input by a user to the electroporation component. In some embodiments, the programmed sequence comprises a plurality of pulses delivered in sequence, wherein each pulse of the plurality of pulses is delivered by at least two active electrodes with one neutral electrode that measures impedance, and wherein a subsequent pulse of the plurality of pulses is delivered by a different one of at least two active electrodes with one neutral electrode that measures impedance.

In some embodiments, the feedback mechanism is performed by either hardware or software. Preferably, the feedback mechanism is performed by an analog closed-loop circuit. Preferably, this feedback occurs every 50 µs, 20 µs, 10 µs or 1 µs, but is preferably a real-time feedback or instantaneous (i.e., substantially instantaneous as determined by available techniques for determining response time). In some embodiments, the neutral electrode measures the impedance in the desired tissue and communicates the impedance to the feedback mechanism, and the feedback mechanism responds to the impedance and adjusts the pulse of energy to maintain the constant current at a value similar to the preset current. In some embodiments, the feedback mechanism maintains the constant current continuously and instantaneously during the delivery of the pulse of energy.

When taken up by a cell, the genetic construct(s) may remain present in the cell as a functioning extrachromosomal molecule. DNA may be introduced into cells, where it is present on a transient basis, in the form of a plasmid or plasmids. Alternatively, RNA may be administered to the cell. It is also contemplated to provide the genetic construct as a linear minichromosome including a centromere, telomeres and an origin of replication. Gene constructs may constitute part of the genetic material in attenuated live microorganisms or recombinant microbial vectors which are administered to subjects. Gene constructs may be part of genomes of recombinant viral vaccines where the genetic material remains extrachromosomal. Genetic constructs include regulatory elements necessary for gene expression of a nucleic acid molecule. The elements include: a promoter, an initiation codon, a stop codon, and a polyadenylation signal. In addition, enhancers are often required for gene expression of the sequence that encodes the target protein or the immunomodulating protein. It is necessary that these elements be operably linked to the sequence that encodes the desired proteins and that the regulatory elements are operable in the individual to whom they are administered.

An initiation codon and a stop codon are generally considered to be part of a nucleotide sequence that encodes the desired protein. However, it is necessary that these elements are functional in the individual to whom the gene construct is administered. The initiation and termination codons must be in frame with the coding sequence.

Promoters and polyadenylation signals used must be functional within the cells of the individual.

Examples of promoters useful to practice the present invention, especially in the production of a genetic vaccine for humans, include but are not limited to promoters from Simian Virus 40 (SV40), Mouse Mammary Tumor Virus (MMTV) promoter, Human Immunodeficiency Virus (MV) such as the BIV Long Terminal Repeat (LTR) promoter, Moloney virus, ALV, Cytomegalovirus (CMV) such as the CMV immediate early promoter, Epstein Barr Virus (EBV), Rous Sarcoma Virus (RSV) as well as promoters from human genes such as human Actin, human Myosin, human Hemoglobin, human muscle creatine and human metalothionein.

Examples of polyadenylation signals useful to practice the present invention, especially in the production of a genetic vaccine for humans, include but are not limited to SV40 polyadenylation signals, bovine growth hormone polyadenylation (bgh-PolyA) signal and LTR polyadenylation signals. In particular, the SV40 polyadenylation signal that is in pCEP4 plasmid (Invitrogen, San Diego, Calif.), referred to as the SV40 polyadenylation signal, is used.

In addition to the regulatory elements required for DNA expression, other elements may also be included in the DNA molecule. Such additional elements include enhancers. The enhancer may be selected from the group including but not limited to: human Actin, human Myosin, human Hemoglobin, human muscle creatine and viral enhancers such as those from CMV, RSV and EBV, Genetic constructs can be provided with mammalian origin of replication in order to maintain the construct extrachromosomally and produce multiple copies of the construct in the cell. Plasmids pVAX1, pCEP4 and pREP4 from Invitrogen (San Diego, Calif.) contain the Epstein Barr virus origin of replication and nuclear antigen EBNA-1 coding region which produces high copy episomal replication without integration.

In some preferred embodiments related to immunization applications, nucleic acid molecule(s) are delivered which include nucleotide sequences that encode a target protein, the immunomodulating protein and, additionally, genes for proteins which further enhance the immune response against such target proteins. Examples of such genes are those which encode other cytokines and lymphokines such as alpha-interferon, gamma-interferon, platelet derived growth factor (PDGF), TNF, GM-CSF, epidermal growth factor (EGF), IL-1, IL-2, 11-4, IL-6, IL-10, IL-12 and IL-15 including IL-15 having the signal sequence deleted and optionally including the signal peptide from IgE.

The compositions used in the methods may further comprise one or more of the following proteins and/or nucleic acid molecules encoding such proteins, as set forth in U.S. Ser. No. 10/139,423, which corresponds to U.S. Publication No. 20030176378, which is incorporated herein by reference: Major Histocompatibility Complex antigens including Major Histocompatibility Complex Class I antigen or Major Histocompatibility Complex Class II antigen; death domain receptors including, but not limited to, Apo-1, Fas, TNFR-1, p55, WSL-1, DR3, TRAMP, Apo-3, AIR, LARD, NGRF, DR4, DR5, KILLER, TRAIL-R2, TRICK2, and DR6; death signals, i.e. proteins that interact with the death domain receptors including, but not limited to FADD, FAP-1, TRADD, RIP, FLICE, and RAIDD; or death signals that include ligands that bind death domain receptors and initiate apoptosis including, but not limited to, FAS-L, and TNF; and mediators that interact with death domain receptors including, but not limited to, FADD, MORT1, and MyD88; toxins including proteins which kill cells such as, but not limited to, insect and snake venoms, bacterial endotoxins such as *Psuedomoneus* endotoxin, double chain ribosome inactivating proteins such as ricin including single chain toxin, and gelonin.

The compositions used in the methods may further comprise one or more of the following proteins and/or nucleic acid molecules encoding such proteins, as set forth in U.S. Ser. No. 10/560,650, which corresponds to U.S. Publication No. 20070041941, which is incorporated herein by reference: IL-15 including fusion proteins comprising non-IL-15 signal peptide linked to IL-15 protein sequences such as fusion proteins comprising an IgE signal peptide linked to IL-15 protein sequences, CD40L, TRAIL; TRAILrecDRC5, TRAIL-R2, TRAIL-R3, TRAIL-R4, RANK, RANK LIGAND, Ox40, Ox40 LIGAND, NKG2D, F461811 or MICA, MICB, NKG2A, NKG2B, NKG2C, NKG2E, NKG2F, CD30, CD153 (CD30L), Fos, c-jun, Sp-1, Ap1, Ap-2, p38, p65Rel, MyD88, IRAK, TRAF6, IkB, NIK, SAP K, SAP1, JNK2, JNK1B2, JNK1B1, JNK2B2, JNK2B1, JNK1A2, JNK2A1, JNK3A1, JNK3A2, NF-kappa-B2, p49 splice form, NF-kappa-B2, p100 splice form, NF-kappa-B2, p105 splice form, NF-kappa-B 50K chain precursor, NFkB p50, human IL-1.alpha., human IL-2, human IL-4, murine IL-4, human IL-5, human IL-10, human IL-15, human IL-18, human TNF-.alpha., human TNF-.beta., human interleukin 12, MadCAM-1, NGF IL-7, VEGF, TNF-R, Fas, CD40L, IL-4, CSF, G-CSF, GM-CSF, M-CSF, LFA-3, ICAM-3, ICAM-2, ICAM-1, PECAM, P150.95, Mac-1, LFA-1, CD34, RANTES, IL-8, MIP-1.alpha., E-selecton, CD2, MCP-1, L-selecton, P-selecton, FLT, Apo-1, Fas, TNFR-1, p55, WSL-1, DR3, TRAMP, Apo-3, AIR, LARD, NGRF, DR4 (TRAIL), DR5, KILLER, TRAIL-R2, TRICK2, DR6, ICE, VLA-1, and CD86 (B7.2).

The compositions used in the methods may further comprise one or more of the following proteins and/or nucleic acid molecules encoding such proteins, as set forth in U.S. Ser. No. 10/560,653, which corresponds to U.S. Publication No. 20070104686, which is incorporated herein by reference: Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, and TAP2.

An additional element may be added which serves as a target for cell destruction if it is desirable to eliminate cells receiving the genetic construct for any reason. A herpes thymidine kinase (tk) gene in an expressible form can be included in the genetic construct. The drug gangcyclovir can be administered to the individual and that drug will cause the selective killing of any cell producing tk, thus, providing the means for the selective destruction of cells with the genetic construct.

In order to maximize protein production, regulatory sequences may be selected which are well suited for gene expression in the cells the construct is administered into. Moreover, codons may be selected which are most efficiently transcribed in the cell. One having ordinary skill in the art can produce DNA constructs that are functional in the cells.

In some embodiments, gene constructs may be provided to in order to produce coding sequences for the immunomodulatory proteins described herein linked to IgE signal peptide.

One method of the present invention comprises the steps of administering nucleic acid molecules intramuscularly, intranasally, intraperatoneally, subcutaneously, intradermally, or topically or by lavage to mucosal tissue selected from the group consisting of inhalation, vaginal, rectal, urethral, buccal and sublingual.

In some embodiments, the nucleic acid molecule is delivered to the cells in conjunction with administration of a polynucleotide function enhancer or a genetic vaccine facilitator agent. Polynucleotide function enhancers are described in U.S. Pat. Nos. 5,593,972 and 5,962,428, which are each incorporated herein by reference. Genetic vaccine facilitator agents are described in U.S. Pat. No. 5,739,118, which is incorporated herein by reference. The co-agents that are administered in conjunction with nucleic acid molecules may be administered as a mixture with the nucleic acid molecule or administered separately simultaneously, before or after administration of nucleic-acid molecules. In addition, other agents which may function transfecting agents and/or replicating agents and/or inflammatory agents and which may be co-administered with a polynucleotide function enhancer include growth factors, cytokines and lymphokines such as a-interferon, gamma-interferon, GM-CSF, platelet derived growth factor (PDGF), TNF, epidermal growth factor (EGF), IL-1, IL-2, IL-4, IL-6, IL-10, IL-12 and IL-15 as well as fibroblast growth factor, surface active agents such as immune-stimulating complexes (ISCOMS), LPS analog including monophosphoryl Lipid A (WL), muramyl peptides, quinone analogs and vesicles such as squalene and squalene, and hyaluronic acid may also be used administered in conjunction with the genetic construct. In some embodiments, an immunomodulating protein may be used as a polynucleotide function enhancer. In some embodiments, the nucleic acid molecule is provided in association with poly(lactide-co-glycolide) (PLG), to enhance delivery/uptake.

The pharmaceutical compositions according to the present invention comprise about 1 nanogram to about 2000 micrograms of DNA. In some preferred embodiments, pharmaceutical compositions according to the present invention comprise about 5 nanograms to about 1000 micrograms of DNA. In some preferred embodiments, the pharmaceutical compositions contain about 10 nanograms to about 800 micrograms of DNA. In some preferred embodiments, the pharmaceutical compositions contain about 0.1 to about 500 micrograms of DNA. In some preferred embodiments, the pharmaceutical compositions contain about 1 to about 350 micrograms of DNA. In some preferred embodiments, the pharmaceutical compositions contain about 25 to about 250 micrograms of DNA. In some preferred embodiments, the pharmaceutical compositions contain about 100 to about 200 microgram DNA.

The pharmaceutical compositions according to the present invention are formulated according to the mode of administration to be used. In cases where pharmaceutical compositions are injectable pharmaceutical compositions, they are sterile, pyrogen free and particulate free. An isotonic formulation is preferably used. Generally, additives for isotonicity can include sodium chloride, dextrose, mannitol, sorbitol and lactose. In some cases, isotonic solutions such as phosphate buffered saline are preferred. Stabilizers include gelatin and albumin. In some embodiments, a vasoconstriction agent is added to the formulation.

According to some embodiments of the invention, methods of inducing immune responses against an immunogen are provided by delivering a combination of the immunogen and IL-28 or functional fragments thereof to an individual. The vaccine may be a live attenuated vaccine, a recombinant vaccine or a nucleic acid or DNA vaccine.

The present invention is useful to elicit enhanced immune responses against a target protein, i.e. proteins specifically associated with pathogens, allergens or the individual's own "abnormal" cells. The present invention is useful to immunize individuals against pathogenic agents and organisms such that an immune response against a pathogen protein provides protective immunity against the pathogen. The present invention is useful to combat hyperproliferative diseases and disorders such as cancer by eliciting an immune response against a target protein that is specifically associated with the hyperproliferative cells. The present invention is useful to combat autoimmune diseases and disorders by eliciting an immune response against a target protein that is specifically associated with cells involved in the autoimmune condition.

According to some aspects of the present invention, DNA or RNA that encodes a target protein and immunomodulating protein is introduced into the cells of tissue of an individual where it is expressed, thus producing the encoded proteins. The DNA or RNA sequences encoding the target protein and immunomodulating protein are linked to regulatory elements necessary for expression in the cells of the individual. Regulatory elements for DNA expression include a promoter and a polyadenylation signal. In addition, other elements, such as a Kozak region, may also be included in the genetic construct.

In some embodiments, expressible forms of sequences that encode the target protein and expressible forms of sequences that encode both immunomodulating proteins are found on the same nucleic acid molecule that is delivered to the individual.

In some embodiments, expressible forms of sequences that encode the target protein occur on a separate nucleic acid molecule from expressible forms of sequences that encode the immunomodulatory protein. In some embodiments, expressible forms of sequences that encode the target protein and expressible forms of sequences that encode one or more of the immunomodulatory proteins occur on a one nucleic acid molecule that is separate from the nucleic acid molecule that contain expressible forms of sequences that encode the immunomodulating protein. Multiple different nucleic acid molecules can be produced and delivered according to the present invention.

The nucleic acid molecule(s) may be provided as plasmid DNA, the nucleic acid molecules of recombinant vectors or as part of the genetic material provided in an attenuated vaccine. Alternatively, in some embodiments, the target protein and immunomodulating protein may be delivered as a protein in addition to the nucleic acid molecules that encode them or instead of the nucleic acid molecules which encode them.

Genetic constructs may comprise a nucleotide sequence that encodes a target protein or an immunomodulating protein operably linked to regulatory elements needed for gene expression. According to the invention, combinations of gene constructs that include one construct that comprises an expressible form of the nucleotide sequence that encodes a target protein and one construct that includes an expressible form of the nucleotide sequence that encodes an immunomodulating protein are provided. Delivery into a living cell of the DNA or RNA molecule(s) that include the combination of gene constructs results in the expression of the DNA or RNA and production of the target protein and one or more immunomodulating proteins. An enhanced immune response against the target protein results.

The present invention may be used to immunize an individual against pathogens such as viruses, prokaryote and pathogenic eukaryotic organisms such as unicellular pathogenic organisms and multicellular parasites. The present invention is particularly useful to immunize an individual against those pathogens which infect cells and which are not encapsulated such as viruses, and prokaryote such as gonorrhea, listeria and shigella. In addition, the present invention is also useful to immunize an individual against protozoan pathogens that include a stage in the life cycle where they are intracellular pathogens. Table 1 provides a listing of some of the viral families and genera for which vaccines according to the present invention can be made. DNA constructs that comprise DNA sequences that encode the peptides that comprise at least an epitope identical or substantially similar to an epitope displayed on a pathogen antigen such as those antigens listed on the tables are useful in vaccines. Moreover, the present invention is also useful to immunize an individual against other pathogens including prokaryotic and eukaryotic protozoan pathogens as well as multicellular parasites such as those listed on Table 2.

Tables

TABLE 1

| Viruses |
|---|
| Picornavirus Family |
| Genera: |
| Rhinoviruses: (Medical) responsible for ~50% cases of the common cold. |
| Etheroviruses: (Medical) includes polioviruses, coxsackieviruses, echo viruses, and human enteroviruses such as hepatitis A virus. |
| Apthoviruses: (Veterinary) these are the foot and mouth disease viruses. |
| Target antigens: VP1, VP2, VP3, VP4, VPG |
| Calcivirus Family |
| Genera: |
| Norwalk Group of Viruses: (Medical) these viruses are an important causative agent of epidemic gastroenteritis. |
| Togavirus Family |
| Genera: |
| Alphaviruses: (Medical and Veterinary) examples include Sindbis virus, RossRiver virus |
| and Venezuelan Eastern & Western Equine encephalitis viruses. |
| Reovirus: (Medical) Rubella virus. |
| Flariviridae Family |
| Examples include: (Medical) dengue, yellow fever, Japanese encephalitis, St Louis encephalitis and tick borne encephalitis viruses. West Nile virus(Genbank NCC01563, AF533540, AF404757, AF404756, AF404755, AF404754, AF404753, AF481864, M12294, AF317203, AF196835, AF260969, AF260968, AF260967, AF206518 and AF202541) |
| Representative Target antigens: E NS5 C |
| Hepatitis C Virus: (Medical) these viruses are not placed in a family yet but are believed to be either a togavirus or a flavivirus. Most similarity is with togavirus family. |
| Coronavirus Family: (Medical and Veterinary) |
| Infectious bronchitis vims (poultry) |
| Porcine transmissible gastroenteric virus (pig) |
| Porcine hemagglutinating encephalomyelitis virus (pig) |
| Feline infectious peritonitis virus (cals) |
| Feline enteric coronavirus (cat) |
| Canine coronavirus (dog) |
| SARS associated coronavirus |
| The human respiratory coronaviruses cause about 40% of cases of common cold. EX. 224E, OC43 Note - coronaviruses may cause non-A, B or C hepatitis |
| Target antigens: E1 - also called M or matrix protein E2 also called S or Spike protein E3 - also called BE or hemagglutin-elterose glycoprotein (not present in all coronaviruses) N- |

TABLE 1-continued

Viruses nucleocapsid
Rhabdovirus Family
Genera:
Vesiculovirus, Lyssavirus:(medical and veterinary) rabies
Target antigen: G protein, N protein
Filoviridae Family: (Medical)
Hemorrhagic fever viruses such as Marburg and Ebola virus
Paramyxovirus Family:
Genera:
Paramyxovirus: (Medical and Veterinary) Mumps virus, New Castle
disease virus (important pathogen in chickens)
Morbillivirus: (Medical and Veterinary) Measles, canine distemper
Pneumovirus: (Medical and Veterinary) Respiratory syncytial virus
Orthomyxovirus Family (Medical) The Influenza virus
Bunyavirus Family
Genera:
Bunyavirus: (Medical) California encephalitis, La Crosse
Phlebovirus: (Medical) Rift Valley Fever
Hantavirus: Puremala is a hemahagin fever virus
Nairvirus (Veterinary) Nairobi sheep disease
Also many unassigned bungaviruses
Arenavirus Family (Medical) LCM, Lassa fever virus
Reovirus Family
Genera:
Reovirus: a possible human pathogen
Rotavirus: acute gastroenteritis in children
Orbiviruses: (Medical and Veterinary) Colorado Tick fever,
Lcbombo (humans) equine encephalosis, blue tongue
Retroyirus Family
Sub-Family:
Oncorivirinal: (Veterinary) (Medical) feline leukemia virus, HTLVI
and HTLVII
Lentivirinal: (Medical and Veterinary) HIV, feline immunodeficiency
virus, equine infections, anemia virus
Spumavirinal Papovavirus Family
Sub-Family:
Polyomaviruses: (Medical) BKU and JCU viruses
Sub-Family:
Papillomavirus: (Medical) many viral types associated with cancers
or malignant progression of papilloma.
Adenovirus (Medical) EX AD7, ARD., O.B. - cause respiratory
disease - some adenoviruses such as 275 cause enteritis
Parvovirus Family (Veterinary)
Feline parvovirus: causes feline enteritis
Feline panleucopeniavirus
Canine parvovirus
Porcine parvovirus
Herpesvirus Family
Sub-Family:
alphaherpes viridue
Genera:
Simplexvirus (Medical)
HSVI (Genbank X14112, NC001806),
HSVII (NC001798)
Varicella zoster: (Medical Veterinary)
Pseudorabies
varicella zoster
Sub-Family
betaherpesviridae
Genera:
Cytomegalovirus (Medical)
HCMV
Muromegalovirus
Sub-Family.
Gammaherpesviridae
Genera:
Lymphocryptovirus (Medical)
EBV - (Burkitt's lymphoma)
Poxvirus Family
Sub-Family:
Chordopoxviridae (Medical - Veterinary)
Genera:
Variola (Smallpox)
Vaccinia (Cowpox)
Parapoxvirus - Veterinary
Auipoxvirus - Veterinary
Capripoxvirus
Leporipoxvirus

TABLE 1-continued

Viruses

Suipoxviru's
Sub-Family:
Entemopoxviridue
Hepadnavirus Family
Hepatitis B virus
Unclassified Hepatitis delta virus

TABLE 2

Bacterial pathogens
Pathogenic gram-positive cocci include: pneumococcal; staphylococcal; and streptococcal.
Pathogenic gram-negative cocci include: meningococcal; and gonococcal.
Pathogenic enteric gram-negative bacilli include: enterobacteriaceae; *pseudomonas, acinetobacteria* and *eikenella*, melioidosis; *salmonella*; *shigellosis*; haemophilus; chancroid; brucellosis; tularemia; *yersinia* *(pasteurella)*; *streptobacillus mortiliformis* and *spirillum*; *listeria monocytogenes*; *erysipelothrix rhusiopathiae*; diphtheria, cholera, anthrax; donovanosis (granuloma inguinale); and *bartonellosis*.
Pathogenic anaerobic bacteria include: tetanus; botulism; other clostridia; tuberculosis; leprosy; and other mycobacteria.
Pathogenic spirochetal diseases include: syphilis; - treponematoses: yaws, pinta and endemic syphilis; and leptospirosis.
Other infections caused by higher pathogen bacteria and pathogenic fungi include: actinomycosis; nocardiosis; cryptococcosis, blastomycosis, histoplasmosis and coccidioidomycosis; candidiasis, aspergillosis, and mucormycosis; sporotrichosis; paracoccidiodomycosis, petriellidiosis, torulopsosis, mycetoma, and chromomycosis; and dermatophytosis.
Rickettsial infections include rickettsial and rickettsioses.
Examples of mycoplasma and chlamydial infections include: mycoplasma pneumoniae; lymphogranuloma venereum; psittacosis; and perinatal chlamydial infections.
Pathogenic eukaryotes
Pathogenic protozoans and helminths and infections thereby include: amebiasis; malaria; leishmaniasis; trypanosomiasis; toxoplasmosis; *pneumocystis carinii*; babesiosis; giardiasis; trichinosis; filariasis; schistosomiasis; nematodes; trematodes or flukes; and cestode (tapeworm) infections.

In order to produce a genetic vaccine to protect against pathogen infection, genetic material that encodes immunogenic proteins against which a protective immune response can be mounted must be included in a genetic construct as the coding sequence for the target. Because DNA and RNA are both relatively small and can be produced relatively easily, the present invention provides the additional advantage of allowing for vaccination with multiple pathogen antigens. The genetic construct used in the genetic vaccine can include genetic material that encodes many pathogen antigens. For example, several viral genes may be included in a single construct thereby providing multiple targets.

Tables 1 and 2 include lists of some of the pathogenic agents and organisms for which genetic vaccines can be prepared to protect an individual from infection by them. In some preferred embodiments, the methods of immunizing an individual against a pathogen are directed against human immunodeficiency virus (HIV), herpes simplex virus (HSV), hepatitis C virus (HCV), West Nile Virus (WNV) or hepatitis B virus (HBV).

Another aspect of the present invention provides a method of conferring a protective immune response against hyperproliferating cells that are characteristic in hyperproliferative diseases and to a method of treating individuals suffering from hyperproliferative diseases. Examples of hyperproliferative diseases include all forms of cancer and psoriasis.

It has been discovered that introduction of a genetic construct that includes a nucleotide sequence which encodes an immunogenic "hyperproliferating cell"-associated protein into the cells of an individual results in the production of those proteins in the vaccinated cells of an individual. To immunize against hyperproliferative diseases, a genetic construct that includes a nucleotide sequence that encodes a protein that is associated with a hyperproliferative disease is administered to an individual.

In order for the hyperproliferative-associated protein to be an effective immunogenic target, it must be a protein that is produced exclusively or at higher levels in hyperproliferative cells as compared to normal cells. Target antigens include such proteins, fragments thereof and peptides; which comprise at least an epitope found on such proteins. In some cases, a hyperproliferative-associated protein is the product of a mutation of a gene that encodes a protein. The mutated gene encodes a protein that is nearly identical to the normal protein except it has a slightly different amino acid sequence which results in a different epitope not found on the normal protein. Such target proteins include those which are proteins encoded by oncogenes such as myb, myc, fyn, and the translocation gene bcr/abl, ras, src, P53, neu, trk and EGRF. In addition to oncogene products as target antigens, target proteins for anti-cancer treatments and protective regimens include variable regions of antibodies made by B cell lymphomas and variable regions of T cell receptors of T cell lymphomas which, in some embodiments, are also used target antigens for autoimmune disease. Other tumor-associated proteins can be used as target proteins such as proteins that are found at higher levels in tumor cells including the protein recognized by monoclonal antibody 17-IA and folate binding proteins or PSA.

While the present invention may be used to immunize an individual against one or more of several forms of cancer, the present invention is particularly useful to prophylactically immunize an individual who is predisposed to develop a particular cancer or who has had cancer and is therefore susceptible to a relapse. Developments in genetics and technology as well as epidemiology allow for the determination of probability and risk assessment for the development of cancer in individual. Using genetic screening and/or family health histories, it is possible to predict the probability a particular individual has for developing any one of several types of cancer.

Similarly, those individuals who have already developed cancer and who have been treated to remove the cancer or are otherwise in remission are particularly susceptible to relapse and reoccurrence. As part of a treatment regimen, such individuals can be immunized against the cancer that they have been diagnosed as having had in order to combat a recurrence. Thus, once it is known that an individual has had a type of cancer and is at risk of a relapse, they can be immunized in order to prepare their immune system to combat any future appearance of the cancer.

The present invention provides a method of treating individuals suffering from hyperproliferative diseases. In such methods, the introduction of genetic constructs serves as an immunotherapeutic, directing and promoting the immune system of the individual to combat hyperproliferative cells that produce the target protein.

In treating or preventing cancer, embodiments which are free of cells are particularly useful.

The present invention provides a method of treating individuals suffering from autoimmune diseases and disorders by conferring a broad based protective immune response against targets that are associated with autoimmunity including cell receptors and cells which produce "self"-directed antibodies.

T cell mediated autoimmune diseases include Rheumatoid arthritis (RA), multiple sclerosis (MS), Sjogren's syndrome, sarcoidosis, insulin dependent diabetes mellitus (IDDM), autoimmune thyroiditis, reactive arthritis, ankylosing spondylitis, scleroderma, polymyositis, dermatomyositis, psoriasis, vasculitis, Wegener's granulomatosis, Crohn's disease and ulcerative colitis. Each of these diseases is characterized by T cell receptors that bind to endogenous antigens and initiate the inflammatory cascade associated with autoimmune diseases. Vaccination against the variable region of the T cells would elicit an immune response including CTLs to eliminate those T cells.

In RA, several specific variable regions of T cell receptors (TCRs) that are involved in the disease have been characterized. These TCRs include V.beta.-3, V.beta.-14, V.beta.-17 and Va-17. Thus, vaccination with a DNA construct that encodes at least one of these proteins will elicit an immune response that will target T cells involved in R A. See: Howell, M. D., et al., 1991 Proc. Nat. Acad. Sci. USA 88:10921-10925; Piliard, X., et al, 1991 Science 253:325-329; Williams, W. V., et al., 1992 J Clin. Invest. 90:326-333; each of which is incorporated herein by reference. In MS, several specific variable regions of TCRs that are involved in the disease have been characterized. These TCRs include VIP and Va-10. Thus, vaccination with a DNA construct that encodes at least one of these proteins will elicit an immune response that will target T cells involved in MS. See: Wucherpfennig, K. W., et al., 1990 Science 248:1016-1019; Oksenberg, J. R., et al, 1990 Nature 345:344-346; each of which is incorporated herein by reference.

In scleroderma, several specific variable regions of TCRs that are involved in the disease have been characterized. These TCRs include V.beta.-6, V.beta.-8, V.beta.-14 and Va-16, Va-3C, Va-7, Va-14, Va-15, Va-16, Va-28 and Va-12. Thus, vaccination with a DNA construct that encodes at least one of these proteins will elicit an immune response that will target T cells involved in scleroderma.

In order to treat patients suffering from a T cell mediated autoimmune disease, particularly those for which the variable region of the TCR. has yet to be characterized, a synovial biopsy can be performed. Samples of the T cells present can be taken and the variable region of those TCRs identified using standard techniques. Genetic vaccines can be prepared using this information.

B cell mediated autoimmune diseases include Lupus (SLE), Grave's disease, myasthenia gravis, autoimmune hemolytic anemia, autoimmune thrombocytopenia, asthma, cryoglobulinemia, primary biliary sclerosis and pernicious anemia. Each of these diseases is characterized by antibodies that bind to endogenous antigens and initiate the inflammatory cascade associated with autoimmune diseases. Vaccination against the variable region of antibodies would elicit an immune response including CTLs to eliminate those B cells that produce the antibody.

In order to treat patients suffering from a B cell mediated autoimmune disease, the variable region of the antibodies involved in the autoimmune activity must be identified. A biopsy can be performed and samples of the antibodies present at a site of inflammation can be taken. The variable region of those antibodies can be identified using standard techniques. Genetic vaccines can be prepared using this information.

In the case of SLE, one antigen is believed to be DNA. Thus, in patients to be immunized against SLE, their sera can be screened for anti-DNA antibodies and a vaccine can be prepared which includes DNA constructs that encode the variable region of such anti-DNA antibodies found in the sera.

Common structural features among the variable regions of both TCRs and antibodies are well known. The DNA sequence encoding a particular TCR or antibody can generally be found following well known methods such as those described in Kabat, et al 1987 Sequence of Proteins of Immunological Interest U.S. Department of Health and Human Services, Bethesda, Md., which is incorporated herein by reference. In addition, a general method for cloning functional variable regions from antibodies can be found in Chaudhary, V. K., et al, 1990 Proc. Natl. Acad Sci. USA 87:1066, which is incorporated herein by reference.

In addition to using expressible forms of immunomodulating protein coding sequences to improve genetic vaccines, the present invention relates to improved attenuated live vaccines and improved vaccines flint use recombinant vectors to deliver foreign genes that encode antigens. Examples of attenuated live vaccines and those using recombinant vectors to deliver foreign antigens are described in U.S. Pat. Nos. 4,722,848; 5,017,487; 5,077,044; 5,110,587; 5,112,749; 5,174,993; 5,223,424; 5,225,336; 5,240,703; 5,242,829; 5,294,441; 5,294,548; 5,310,668; 5,387,744; 5,389,368; 5,424,065; 5,451,499; 5,453,364; 5,462,734; 5,470,734; and 5,482,713, which are each incorporated herein by reference. Gene constructs are provided which include the nucleotide sequence that encodes an IL-28 or functional fragments thereof, wherein the nucleotide sequence is operably linked to regulatory sequences that can function in the vaccine to effect expression. The gene constructs are incorporated in the attenuated live vaccines and recombinant vaccines to produce improved vaccines according to the invention.

The present invention provides an improved method of immunizing individuals that comprises the step of delivering gene constructs to the cells of individuals as part of vaccine compositions which include DNA vaccines, attenuated live vaccines and recombinant vaccines. The gene constructs comprise a nucleotide sequence that encodes an IL-28 or functional fragments and that is operably linked to regulatory sequences that can function in the vaccine to effect expression. The improved vaccines result in an enhanced cellular immune response.

EXAMPLES

Example 1

IL-28 is a member of the newest class of interferons, Interferon Lambdas, and has a heterodimeric receptor composed of IL-28Ralpha and IL-10Rbeta. As the IL-10Rbeta chain is also a part of the IL-10 receptor, IL-28 was employed in vaccination studies in hopes of blocking IL-10 binding to its target receptor.

The inclusion of plasmid IL-28 with a plasmid HIV Gag construct significantly augmented the interferon gamma response from mouse splenocytes when compared with mice that were immunized with a composition in which the only plasmid is the Gag plasmid alone. Mice were immunized with empty vector (pVAX), a multi-clade HIV Gag construct (HIV Gag—plasmid HIV Gag 10 µg DNA in 30 µl aqueous solution of sodium citrate bupivacaine) or the HIV Gag construct with an IL-28 plasmid (HIV Gag IL-28—plasmid HIV Gag 10 µg DNA+plasmid IL-28 5 µg DNA in 30 µl aqueous solution of sodium citrate bupivacaine)). As shown in the data in FIG. 1, IL-28 increased the ELISpot number by greater than 7 fold when compared to HIV Gag alone.

Figure 2:
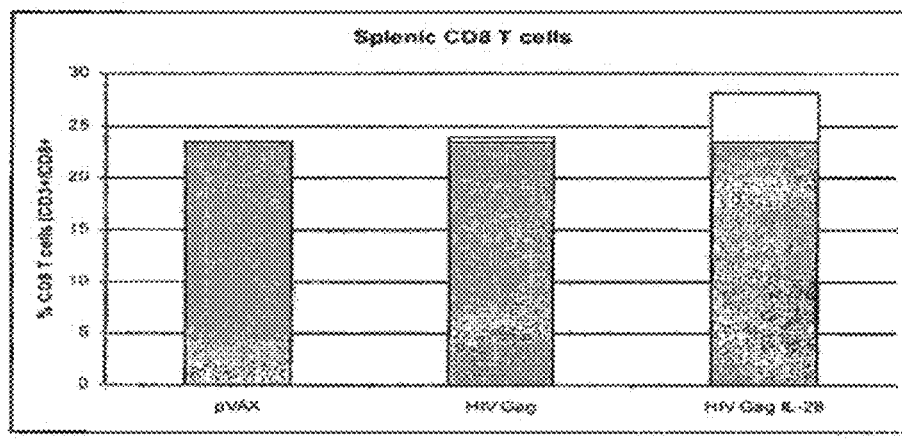
FIG. 2 shows data from analysis of splenocytes in the presence or absence of IL-28 treatment using flow cytometry.

Also surprisingly, analysis of splenocytes using flow cytometry suggested that IL-28 increased splenic CD8 T cells. Mice were immunized as above and the percentage of CD8 T cells was analyzed by flow cytometry. As shown in the data in FIG. 2, the addition of IL-28 increased the percentage of CD8 T cells by 4.72% over mice immunized with pVAX alone, which accounts for an increase of ~20% of total CD8s. Mice that were immunized with the HIV Gag construct alone had an increase of only 0.48% over pVAX mice, accounting for an increase of ~2% of total CD8s. (White bars indicate increase in CD8% over pVAX control)

Thus, while previous attempts at employing interferons as adjuvants in vaccination have had disappointing results, results herein indicate that IL-28 is an effective adjuvant in vaccination, particularly DNA vaccination.

Example 2

Mice were immunized with 1) HIV Gag construct (HIV Gag—plasmid HIV Gag 10 µg DNA in 30 µl aqueous solution of sodium citrate bupivacaine) or 2) the HIV Gag construct with an IL-28 plasmid (HIV Gag IL-28—plasmid HIV Gag 10 µg DNA+plasmid IL-28 3 µg DNA in 30 µl aqueous solution of sodium citrate bupivacaine) or the HIV Gag construct with IL-28 protein (HIV Gag—plasmid HIV Gag 10 µg DNA in 30 µl aqueous solution of sodium citrate bupivacaine plus 40 ng IL-28 protein), or 4) the HIV Gag construct with interferonγ protein (HIV Gag—plasmid HIV Gag 10 µg DNA in 30 µl aqueous solution of sodium citrate bupivacaine plus 40 ng interferonγ protein).

Using ELI Spot, the mice receiving plasmid IL-28 showed an increased anti-Gag immune response compared to HIV Gag alone. Neither IL-28 protein nor interferon γ protein increased anti-Gag immune response compared to HIV Gag alone.

Example 3

Figure 3:
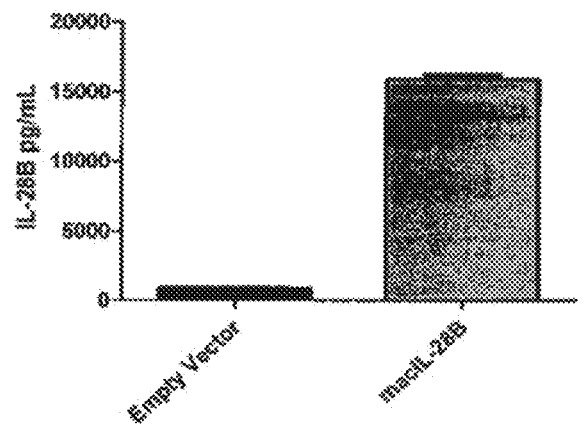
FIG. 3 shows data from the experiments described in Example 3. RD cells were transfected with 3 μg of rhesus macaque IL-28B (macIL-28B) or an empty vector as a control. Supernatants were assayed for the presence of macaque IL-28B via ELISA 48 hours post transfection.

While IL-28B (IFNλ3) has been suggested as being used as a potent adjuvant in mouse studies of DNA vaccination, it's effectiveness in regards to augmenting antigen-specific immune responses has not been studied in larger animals, such as non-human primates. We desired to test a codon and RNA optimized plasmid encoding rhesus macaque IL-28B in vaccination studies against HIV antigens as an immunoadjuvant in these animals. Optimization of the adjuvant plasmid in this method not only increases expression of the encoded gene and stabilizes resulting RNA structures, but also reduces the potential for integration into the host genome as well as eliminating any microRNAs that may have been encoded within the gene, resulting in a high safety profile. Analysis of expression of macaque IL-28B (macIL-28B) was carried out via in vitro transfection of a rhabdosarcoma (RD) cell line with macIL-28B or an empty vector. Supernatants harvested from cells transfected with macIL-28B, but not with empty vector, showed high quantities of macaque IL-28B present at 48 hours post transfection when assayed via ELISA, suggesting high degrees of plasmid expression (FIG. 3).

Figure 4:
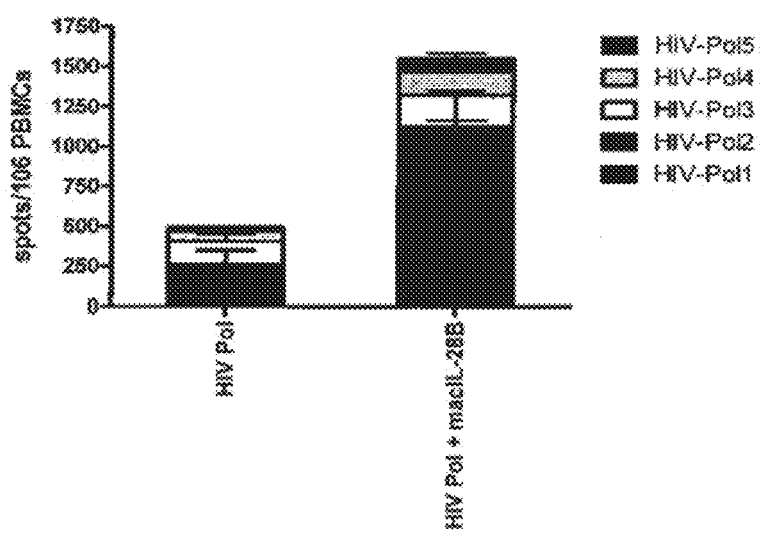
FIG. 4 also shows data from the experiments described in Example 3. Rhesus macaques were immunized twice with a plasmid encoding HIV Pol alone or in combination with a plasmid encoding macaque IL-28B. Addition of macIL-28B increased antigen specific immune responses by ~3 fold when assayed by IFNgamma ELISpot.

Upon seeing high degrees of expression in vitro, we decided to add macIL-28B to an immunization regimen against HIV Pol in rhesus macaques. Addition of IL-2813 lead to a~3 fold increase in HIV Pol specific IFNgamma release as gauged by ELISpot after 2 immunizations (FIG. 4). These data suggest that the macIL-28B plasmid is a novel method of expressing high levels of IL-28B and can be used as an effective immunoadjuvant in a non-human primate model of DNA vaccination.

Example 4

Improving the potency of immune responses is paramount among issues concerning vaccines against deadly pathogens. IL-28B belongs to the newly described Interferon Lambda (IFNλ) family of cytokines, and has not yet been assessed for its potential ability to influence adaptive immune responses or act as a vaccine adjuvant. We compared the ability of plasmid encoded IL-28B to boost immune responses to a multi-clade consensus HIV Gag plasmid during DNA vaccination with that of IL-12. We show here that IL-28B, like IL-12, is capable of robustly enhancing adaptive immunity. Moreover, we describe for the first time how IL-28B reduces Regulatory T cell populations during DNA vaccination, whereas IL-12 increases this cellular subset. We also show that IL-28B, unlike IL-12, is able to increase the percentage of splenic CD8+ T cells in vaccinated animals, and that these cells are more granular and have higher antigen-specific cytolytic degranulation when compared to cells taken from animals that received IL-12 as an adjuvant. Lastly, we report that IL-28B can induce 100% protection from mortality after a lethal influenza challenge. These data suggest that IL-28B is a strong candidate for further studies of vaccine or immunotherapy protocols.

Introduction

Having a comprehensive understanding of the immune system and its components is critical not only for understanding host-pathogen interactions during infections, but also in the context of vaccine development and design. In regards to immune-associated signaling compounds, such as cytokines, vaccination studies may additionally give us a means by which to study how these molecules affect antigen specific immune responses.

DNA vaccination is a safe and effective method of inducing antigen specific immune responses in vivo[1-3] that lends itself to the introduction of immune modulators. The ability to easily add plasmids encoding cytokines into DNA vaccination platforms allows for the simultaneous assessment of how a cytokine may influence adaptive immune responses as well as determining its potential value as a vaccine adjuvant. Furthermore, recent data in nonhuman primates with optimized DNA formulations are showing more promising immune profiles. Improving on these encouraging results is an important goal.

The Interferon Lambda family consists of three recently discovered cytokines: IL-29, IL-28A and IL-28B (IFNλ 1, 2, and 3, respectively)[4-7]. All three cytokines have been shown to be expressed in response to viral infections in vitro, and are secreted primarily by dendritic cells and macrophages[4-7]. Additionally, all three cytokines are classified as Interferons due to the fact that treatment of cells with these cytokines can induce an antiviral state which inhibits viral replication in culture, owing to STAT, IRF and ISGF activation through the IL-28 receptor[4-7]. While receptor expression has been shown on a variety of leukocytes, including T-lymphocytes[8], the relative ability of IL-28 to shape antigen-specific adaptive immune responses has not been extensively studied to this point.

In this study, we have analyzed the ability of IL-28B to act as an adjuvant in a DNA vaccination setting, and compared its ability to augment immune responses with that of IL-12, which is a potent and perhaps best established DNA immunoadjuvant[9-13]. In doing so, we have characterized the impact of IL-28B on the antigen specific adaptive immune response, which has not yet been studied. The inclusion of plasmid encoded IL-28B or IL-12 lead to increased antigen specific cellular immune responses over vaccination with antigen alone, as gauged by IFNγ ELISpot and detection of perforin by flow cytometry. IL-28B, but not IL-12, was further able to increase antigen-specific IgG2a, antigen specific cytolytic degranulation and the percentage of CD8+T cells found in the spleen. Additionally, we found that the IL-28B adjuvant reduced the number of CD4+/CD25$^{hi}$/FoxP3+ (Treg) cells found in the spleens of vaccinated animals, while IL-12 increased the size of this population. Lastly, we show here, when used as an adjuvant for vaccination in mice, IL-28B is able to augment immune responses in such a fashion so as to result in 100% protection from death after a lethal influenza challenge. This study shows that IL-28B may act as an effective adjuvant for cellular immunity in vivo and is the first to describe the differential affects of IL-28B and IL-12 on Treg populations after DNA vaccination. This constitutes the first major analysis of the ability of IL-28B to shape adaptive immune responses in vivo.

Materials and Methods

Plasmids. The IL-12 plasmid encoding murine p35 and p40 proteins has been described[11,14]. Murine IL-28B had a high efficiency leader sequence added to the 5' end of the gene and was synthesized, codon optimized and subsequently subcloned into the pVAX1 backbone by GeneArt (Renensberg, Germany). Plasmids expressing HIV-1 Gag (Gag4Y) were prepared as previously described[15].

Animals. All animals were housed in a temperature-controlled, light-cycled facility at the University of Pennsylvania, and their care was under the guidelines of the National Institutes of Health and the University of Pennsylvania. All animal experiments were performed in accordance with national and institutional guidelines for animal care and were approved by the Institutional Review Board of the University of Pennsylvania.

Immunization of Mice. The quadriceps muscle of 8 week old female BALB/c mice (Jackson Laboratory) were injected 2 times, 2 weeks apart, and electroporated as previously described[16] using the CELLECTRA® adaptive constant current device (VGX Pharmaceuticals, The Woodlands, Tex.). For experiments in mice, the animals (n=4 or 8 per group) were immunized with either 10 μg of pVAX1 or 10 μg of HIV-1 Gag (Gag4Y) or Influenza NP (NP) alone or with varying amounts of murine IL-12 or murine IL-28B plasmid, depending on the experiment. Co-administration of various gene plasmids involved mixing the designated DNA plasmids before injection in 0.25% bupivicaine-HCL (Sigma) in isotonic citrate buffer to a final volume of 30 μl.

ELISpot. Both IFN-γ and IL-4 ELISpot was performed to determine antigen specific cytokine secretion from immunized mice. ELISpots were carried out per manufacturers protocols (R&D Systems) using 96-well plates (Millipore). $2 \times 10^5$ splenocytes from immunized mice were added to each well of the plate and stimulated overnight at 37° C., 5% $CO_2$, in the presence of RIO (negative control), concanavalin A (positive control), or specific peptide (HIV-1 Gag) antigens (10 μg/ml). HIV-1 Consensus Gag Clade C 15-mer peptides spanning the entire protein, overlapping by 11 amino acids, were acquired from the AIDS Reagent and Reference Repository (Frederick, Md.).

Cell Culture and Staining for Flow Cytometry. Splenocytes harvested from immunized mice were washed and then resuspended with RIO media to a final concentration of $10^7$ cells/ml. Cells were seeded into 96 well plates in a volume of 100 µl and an additional 100 µl of media alone (negative control), media containing HIV-1 Gag Consensus Clade C peptides or media containing PMA and Ionomycin (positive control) was then added and plates were place at 37° C. In cultures being used to measure degranulation, anti-CD107a PE was added at this time as an enhanced stain. Cultures used to measure intracellular perforin levels did not receive this antibody. For these cultures, ten minutes after the addition of media, peptide or PMA/Ionomycin, $Mg^{+2}$ and EGTA were added to cultures to a final concentration of 6 mM and 8 mM, respectively to inhibit calcium-dependent cytolytic degranulation[17]. All cultures were allowed to incubate at 37° C. for 6 hours. At the end of this incubation period, plates were spun down and washed twice with PBS. Cells were then stained with a violet dye for viability (LIVE/DEAD Violet Viability Dye, Invitrogen) for 10 minutes at 37° C. After washing as above with PBS, cells were stained externally with anti-CD4 PerCPCy5.5 (BD Bioscience) and anti-CD8 APCCy7 (BD Bioscience) at 4° C., followed by fixing and permeabilization (Cytofix/Cytoperm Kit, BD Bioscience). Anti-CD3 PE-Cy5 (BD Bioscience) and anti-Perforin APC (eBioscience) were added and cells were incubated again at 4° C. Cells were given a final wash with PBS and fixed in PFA at a final concentration of 1%. For flow cytometry involving $CD4+/CD25^{hi}/FoxP3+$ cells, the Mouse Regulatory T Cell staining kit was employed (eBioscience). External staining was carried out as above with anti-CD4 FITC and anti-CD25 APC. Fixation, permeabilization and internal staining were also carried out as above using anti-FoxP3 PE.

Influenza Challenge. 28 days post immunization, anaesthetized mice were intranasally inoculated with 10 LD50 of A/Puerto Rico/8/34 in 30 µl PBS[16]. All murine challenge groups were comprised of 8 mice per group. After challenge, clinical signs and mortality were recorded daily for 14 days.

Statistics. Data are presented as the mean±Standard Error of the Mean (SE) calculated from data collected from at least three independent experiments. Where appropriate, the statistical difference between immunization groups was assessed by using a paired Student's t Test and yielded a specific p value for each experimental group. Comparisons between samples with a p value<0.05 were considered to be statistically different and therefore significant.

Results

Plasmids Encoding Murine IL-12 and IL-28B Express and Secrete Protein

There is a constant need for discovery of new and improved adjuvants for vaccination against various viral pathogens. In the past, IL-12 has been shown to be a potent adjuvant when employed in vaccination studies[9-13]. IL-28B has not yet been used for this purpose. In order to compare the relative abilities of these cytokines to augment antigen-specific immune responses, we constructed plasmids encoding murine IL-12[11] and murine IL-28B for use in our DNA vaccination studies (FIGS. 5A and 5B). To confirm whether these constructs expressed IL-12 and IL-28B, we tested them in vitro via transfection of HEK 293T cells with 3 µg of plasmid. Cells were subsequently lysed and lysates were used in Western Blots to test for protein expression. Blots for murine IL-12p40 and murine IL-28B proteins show that both constructs are expressed well in vitro (FIG. 6A). To examine cytokine secretion to the extracellular environment, cell supernatants were obtained 48 hours post transfection. ELISAs to detect the active IL-12 p35/p40 heterodimer and the IL-28B protein from transfected cell culture supernatants were carried out. As shown in FIG. 6B, IL-12 and IL-28B were both observed to be present at a concentration of roughly 10,000 µg/ml in transfected culture supernatants. Upon confirming the expression and release of both cytokines from transfected cells, we began vaccination studies to test the ability of these cytokines to adjuvant antigen-specific immune responses.

IL-28B Adjuvants HIV Gag-Specific IFNγ Release After Vaccination

Figure 7A:
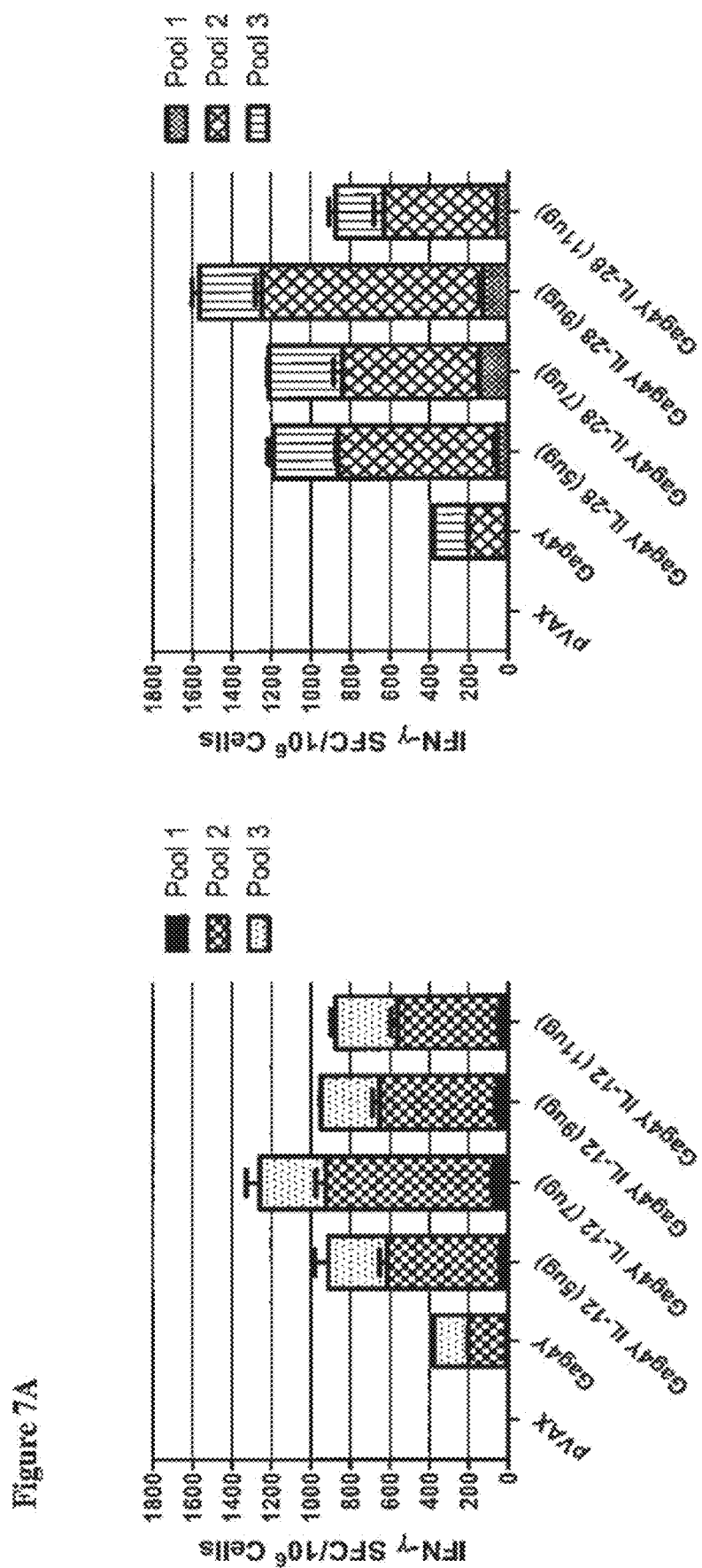

In order to determine whether or not IL-28B had the potential to function as an immunoadjuvant, we used it in DNA vaccination studies in combination with a plasmid encoding a multi-clade consensus HIV-1 Gag protein (Gag4Y) as our target antigen. In order to have a measure of comparison of the potency of the adjuvant affects of IL-28B, we compared it to a cytokine that is frequently employed as an adjuvant in vaccinations due to the fact that it has previously been shown to have very potent immunoadjuvant affects: IL-12[9-13]. To that end, groups of 8 week old Balb/c mice (n=4 per group) were immunized intramuscularly in the right rear quadricep with 10 µg of empty pVAX vector (control) or 10 µg of HIV Gag4Y construct alone, followed by electroporation. Additional groups received 10 µg of HIV Gag4Y in combination with either IL-28B or IL-12 at varying doses, also followed by electroporation. Results of an IFNγ ELISpot assay show that while immunization with Gag4Y alone was able to induce a cellular immune response in the mice 18 400 SFU per million splenocytes), inclusion of IL-28B was able to further increase Gag-specific IFNγ release at all doses tested several fold (FIG. 7A). Optimal adjuvant affects of IL-28B (3 to 4-fold over Gag4Y alone) were seen at a range of 7 to 9 µg (FIG. 7A), leading us to use this dose for further experiments. IL-12 also increased Gag-specific IFNγ release in this assay by just over 3-fold in the same range of doses as IL-28B (FIG. 7A). Analysis of each assay showed that responses were mediated predominantly by CD8+ T cells (>85% total response) and that this profile was not influenced by the presence of absence of adjuvant during vaccination (data not shown). These results suggest that IL-28B can, indeed, be used to bolster antigen specific immune responses during vaccination, with increases in IFNγ release comparable or greater than those seen with IL-12 which is an established, potent immunoadjuvant.

Upon confirming that IL-28B could be used to increase the cellular immune response via increased release of the Th1-associated cytokine IFNγ, we next endeavored to determine if this adjuvant could affect the release of a prototypical Th2 cytokine. Thus we employed an IL-4 ELISpot in the same fashion as above to observe how IL-28B might be influencing the release of this Th2 associated cytokine. Interestingly, the inclusion of IL-12 in vaccination resulted in increases in Gag-specific IL-4 release at all doses tested, ranging from ~200 to ~600 SFU (FIG. 7B). The optimal doses for IL-12 in the IFNγ ELISpot assay resulted in ~400 to ~450 SFU in the IL-4 ELISpot assay, while the inclusion of IL-28B did not show this type of affect. Instead, inclusion of IL-28B in vaccination resulted in IL-4 release that was quite similar to the HIV Gag4Y construct alone (FIG. 7B), suggesting that IL-28B does not increase IL-4 release concominant with increased IFNγ release at these doses. Thus, IL-28B may be thought of as inducing a more "pure" Th 1-associated cytokine profile during vaccination when compared with IL-12 in that it induces IFNγ (Th1 associated) release but not IL-4 (Th2 associated) release.

IL-28B but not IL-12 Increases HIV Gag Specific IgG2a

Figure 8A:
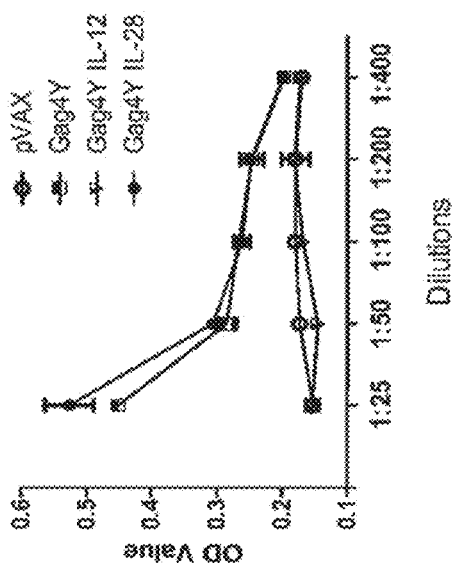
FIGS. 8A, 8B and 8C show HIV Gag Specific IgG in sera from vaccinated animals. Sera from control (pVAX) or immunized animals (n=4) was assayed for the presence of HIV Gag specific antibodies via ELISA one week post immunization.
Figure 8C:
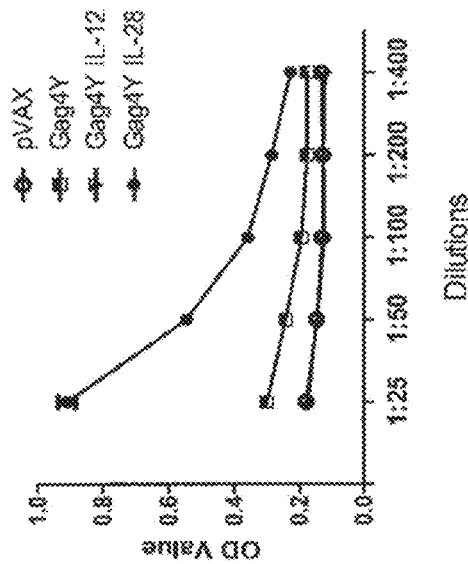
Figure 8B:
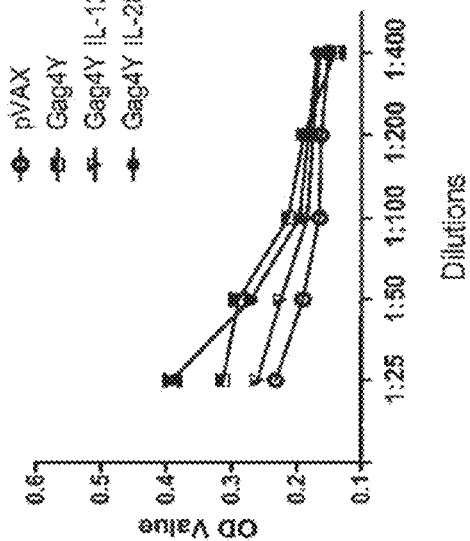

As an effective vaccination against a viral pathogen may necessitate both a cellular and humoral immune response, we decided to examine the relative abilities of IL-28B and IL-12 to augment the level of circulating HIV Gag-specific antibodies when employed as adjuvants during vaccination. In order to accomplish this, we tested sera taken from immunized mice in antigen-specific ELISAs. Inclusion of IL-12 or IL-28B in conjunction with the HIV Gag4Y construct resulted in markedly different antibody responses, as shown in FIG. 8. In regards to total Gag-specific IgG, immunization with the Gag4Y construct together with the IL-28B construct lead to a small increase in levels of antigen-specific antibodies when compared to immunization with Gag4Y alone at the lowest dilution tested (1:25) (FIG. 8A). However, inclusion of IL-12 with Gag4Y immunization actively suppressed antigen-specific IgG, with values reading very similar to those of control (pVAX) mice. This affect of IL-12 is a phenomenon that has been reported previously in DNA vaccination[14], and is supported in the current study as well. We next examined different subtypes of IgG, including IgG1 and IgG2a to determine additional effects on immune polarization. The IgG1 isotype is associated with Th2 skewing in mice while IgG2a is associated with Th1 skewing[18]. Regardless of the inclusion of adjuvant, DNA vaccination did not seem to augment Gag-specific IgG1 antibody levels in any group in our assay (FIG. 8B). However, the inclusion of IL-28B in vaccination lead to a greater than 2-fold increases in IgG2a when compared with sera from mice vaccinated with HIV Gag4Y alone (FIG. 8C). Additionally, IL-12 continued to suppress antibody responses in this assay, as evidenced by the fact that no increase in IgG2a was seen in the IL-12 group when compared to the control (pVAX) group. Thus IL-28B seems to be able to increase antigen specific humoral immune responses in a heavily Th1-biased fashion, which is in agreement with its affect on the cellular immune response (FIGS. 7A and 7B).

IL-28B Decreases Splenic CD4+/CD25$^{hi}$/FoxP3+ Cells, while IL-12 Increases Them IL-28B is a member of the newly described IFN λ family, and thus is also known as IFN λ3[18-21]. Other members of the IFN λ family include IL-28A (IFN λ2) and IL-29 (IFN λ1)[18-21]. A previous study has suggested that IL-29 may play a role in immune suppression and tolerance in that it may drive dendritic cells to specifically induce the proliferation of CD25$^{hi}$/FoxP3+ CD4+ T cells (Treg cells) in response to IL-25. The induction or expansion of Treg cells could be considered a drawback to vaccination strategies within certain settings, and the ability of IL-28B to influence this subpopulation of CD4+ T cells has not previously been studied. As IL-28B falls into the same IFN family as IL-29, we addressed the possibility that it may exert similar affects on the Treg cell population. Additionally, we looked at the ability of IL-12 to affect Tregs in this type of vaccination setting, which has not been previously examined.

Figure 9A:
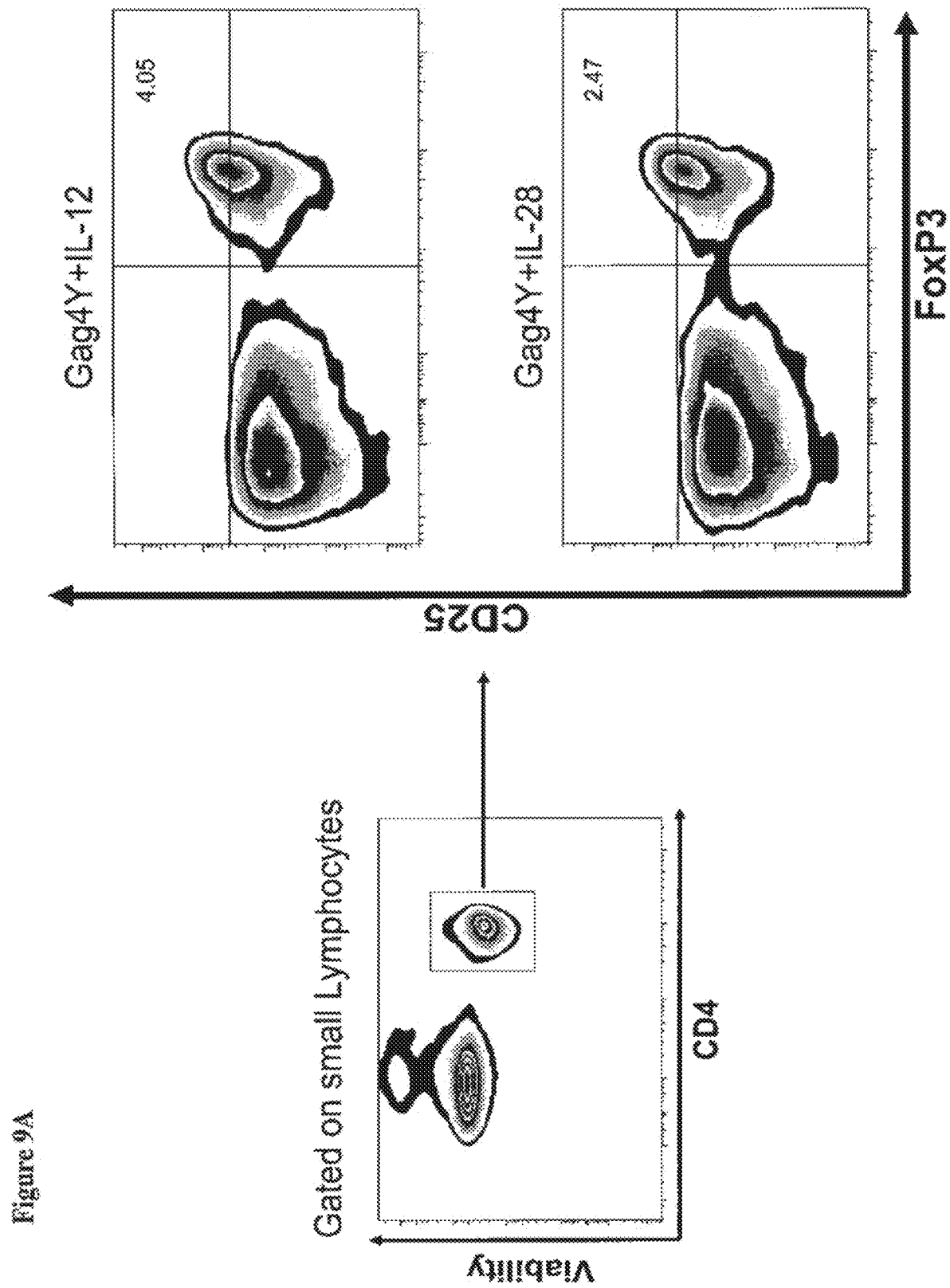
FIGS. 9A and 9B show differential induction of regulatory T Cells and TGFβ secretion during immunization. The presence of Regulatory T cells (CD4+/CD25$^{hi}$/FoxP3+) was assayed from isolated splenocytes from all groups (n=4)via flow cytometry (FIG. 9A). Analysis of flow cytometry shows differences in TReg populations, while analysis of cytokine secretion from these cells shows differences in TGFβ release (FIG. 9B). p values reflect comparisons between mice vaccinated with Gag4Y alone with mice vaccinated with Gag4Y plus IL-12 or IL-28B.
Figure 9B:
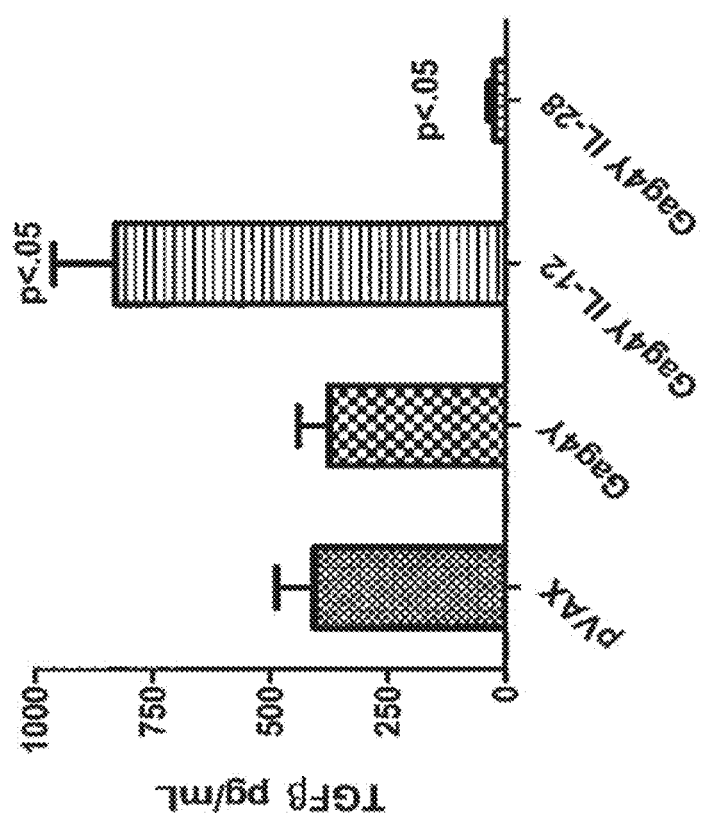
Figure 9B:
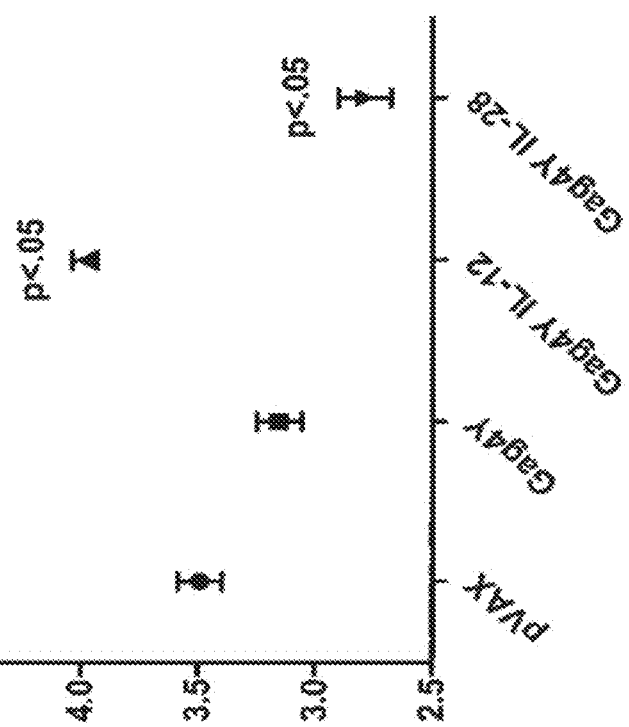
Figure 10A:
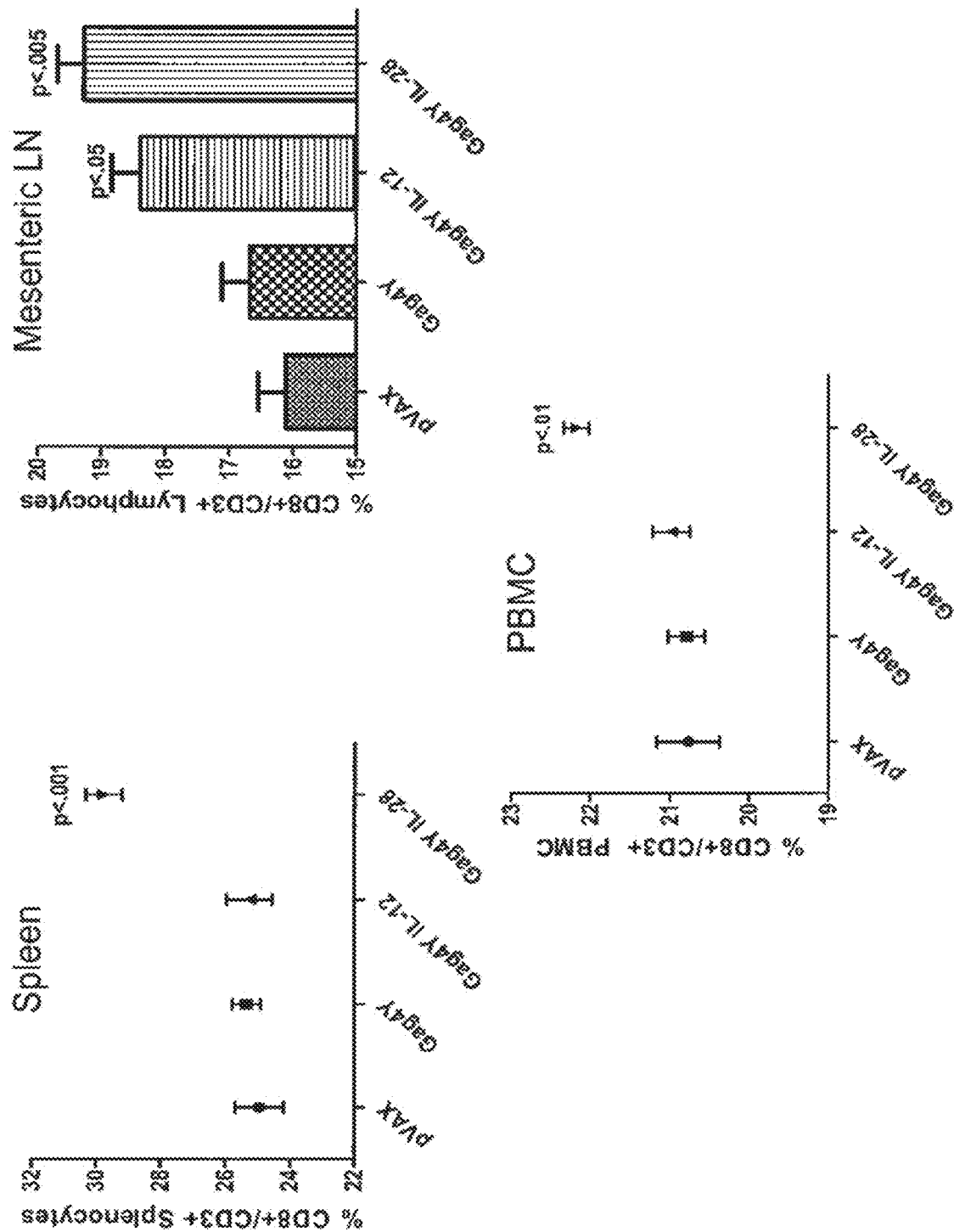
FIGS. 10A, 10B and 10C show changes in CD8+ T Cell populations, granularity and degranulation. The percentage of CD8+ T cells (CD3+/CD8+) was assessed via flow cytometry in the spleen and mesenteric lymphnodes (FIG. 10A). Antigen specific induction of perforin in CD8+ T cells was analyzed by flow cytometry via comparison of unstimulated cells (NP) with cells stimulated with HIV Gag peptides (Peptide). Results from a single experiment are shown (FIG. 10B) and averages for all experiments are graphed (FIG. 10C). Antigen specific cytolytic degranulation was measured via stimulation with peptide in the presence of an antibody to CD107a, followed by analysis using flow cytometry (FIG. 10C). p values reflect comparisons between mice vaccinated with Gag4Y alone with mice vaccinated with Gag4Y plus IL-12 or IL-28B.
Figure 10B:
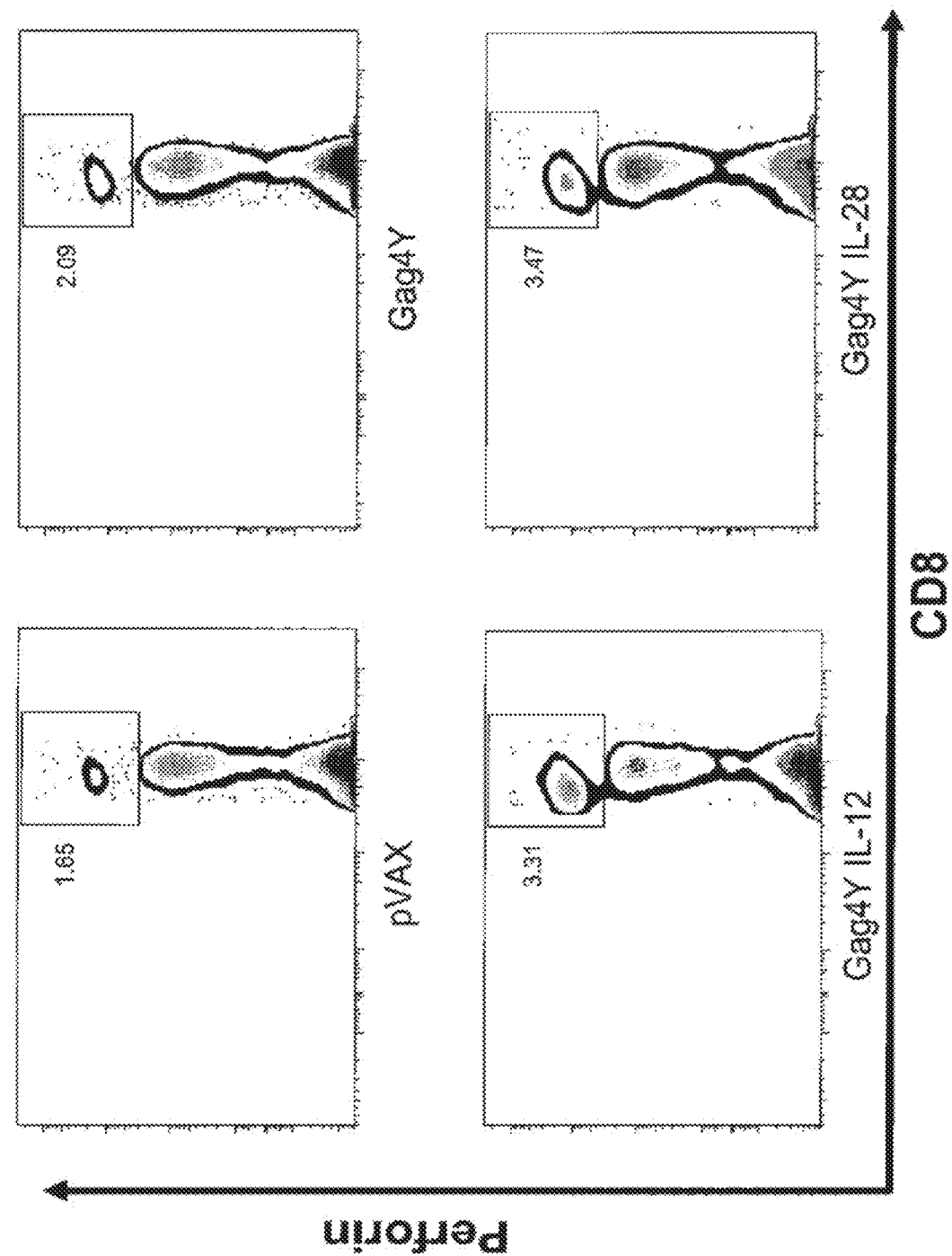

By looking at the expression of CD4, CD25 and FoxP3 via flow cytometry (FIG. 9A), we were able to study the impact of vaccination with and without cytokine adjuvants on Treg populations in immunized mice. The results of this analysis show that immunization with the HIV Gag4Y construct alone resulted in a small but not statistically significant decrease in the percentage of splenic Tregs from vaccinated mice (FIG. 10B). This result is consistent with a previous report describing a similar change in Treg populations after vaccination[20]. Inclusion of cytokine adjuvants in vaccination dramatically altered Treg populations in varying fashions. Interestingly, the employment of IL-12 as an immunoadjuvant significantly increased the number of splenic Tregs in immunized mice when compared with mice vaccinated with the HIV Gag4Y construct alone (FIG. 9B). This is the first time this phenomenon has been reported in a vaccination setting and may constitute a previously unrealized phenotype of IL-12 as an adjuvant for immunization. Also of considerable interest was the fact that the inclusion of IL-28B as an immunoadjuvant for vaccination caused a statistically significant decrease in the number of splenic Tregs when compared to vaccination with HIV Gag4Y alone (FIG. 9B). This is the first time this ability of IL-28B has been described and may be viewed as significant benefit of this cytokine when it is used as an adjuvant for vaccination. Moreover, it suggests the possibility that while they are in the same IFN family, there may be key differences between IL-28B and IL-29.

Splenocytes from Mice that Received IL-28B Secrete Less TGFβ

We reasoned that it was possible that the inclusion of IL-12 or IL-28B in vaccination may have been phenotypically altering normal CD4+ T cells to look like Tregs, instead of inducing the expansion of fully functional Tregulatory cells. Therefore, in order to determine if these cells were functioning as Tregs in addition to phenotypically resembling Tregs, we measured the ability of splenocytes from vaccinated mice to produce TGFβ, which is recognized as one of the major mediators of Treg-based non-contact immunosuppression[21]. To accomplish this, we cultured splenocytes from each group of mice for 48 hours with a combination of PMA and Ionomycin in order to determine TGFβ release from activated cells. At the end of this time period, supernatants were taken from cell cultures and were used in ELISAs to detect TGFβ. As shown in FIG. 9B, activation of splenocytes isolated from mice that received IL-12 as an adjuvant resulted in a statistically significant increase in TGFβ production when compared to mice that received Gag4Y alone (FIG. 9B). This result suggests that the differences in Treg numbers observed via flow cytometry between mice that received IL-12 and mice that received HIV Gag4Y alone are correctly identifying Treg populations. Additionally, splenocytes isolated from mice that received IL-28B as an adjuvant produced significantly less TGF β when activated by PMA and Ionomycin (FIG. 9B). This, again, supports the flow cytometry data suggesting that there are differences in Treg populations in mice that received IL-28B compared to mice that received HIV Gag4Y alone.

As IL-2 is a key cytokine in the induction and expansion of Tregs[21], we reasoned that differences in Treg populations between vaccinated groups could be due to differential production of IL-2. In order to test this possibility we again measured cytokine release from activated splenocytes isolated from each group. Analysis of IL-2 output from these cells show no significant difference between any of the groups (data not shown), suggesting that there is an alternate mechanism responsible for differences in Treg populations seen after DNA vaccination.

IL-28B but not IL-12 Increases Splenic CD8+ T Cells

Upon determining that IL-28B could affect the amount of splenic Tregs, we decided to investigate whether or not this adjuvant had similar affects on other cell types after vaccination. To that end, splenocytes from control and vaccinated mice were analyzed for the presence of CD8 T cells (CD3+/CD8+) by flow cytometry. As shown in FIG. 10A, the percentage of CD8 T cells in the spleens of control (pVAX) mice were not significantly different than mice who received the Gag4Y construct alone, or the Gag4Y construct with the IL-12 adjuvant. However, mice that received IL-28B as an adjuvant showed significantly higher percentages of CD8 T cells in the spleen when compared with all other groups, suggesting that IL-28B has the ability to expand the splenic CD8+ T cell population after immunization. In order to determine whether this affect of IL-28B was restricted to the spleen or could be seen in other lymphoid organs and peripheral blood, we next analyzed lymphocytes isolated from the mesenteric lymph nodes (MLN) as well as circulating PBMCs from each group of mice. Mice immunized with the HIV Gag4Y construct alone showed a small but not statistically significant increase in the number of CD8+ T cells found in MLN when compared to control mice. Mice that received IL-12 as an adjuvant showed increased numbers of CD8+ T cells in MLN when compared to mice that received Gag4Y alone, and this increase was able to reach statistical significance (FIG. 10A). Mice that received IL-28B in conjunction with the HIV Gag4Y construct during immunization had slightly higher increases in CD8+ T cell percentages, which reached an impressive statistical significance ($p<0.005$). Lymphocytes isolated from peripheral blood showed increases in CD8+ T cell populations only in the group that received the IL-28B adjuvant, which is reminiscent of the pattern seen in the spleen (FIG. 10A). These results indicate that IL-28B, but not IL-12, increases the size of CD8+ T cell populations in the spleen and peripheral blood of immunized mice while both adjuvants are able to increase CD8+ T cells in MLN.

Figure 10C:
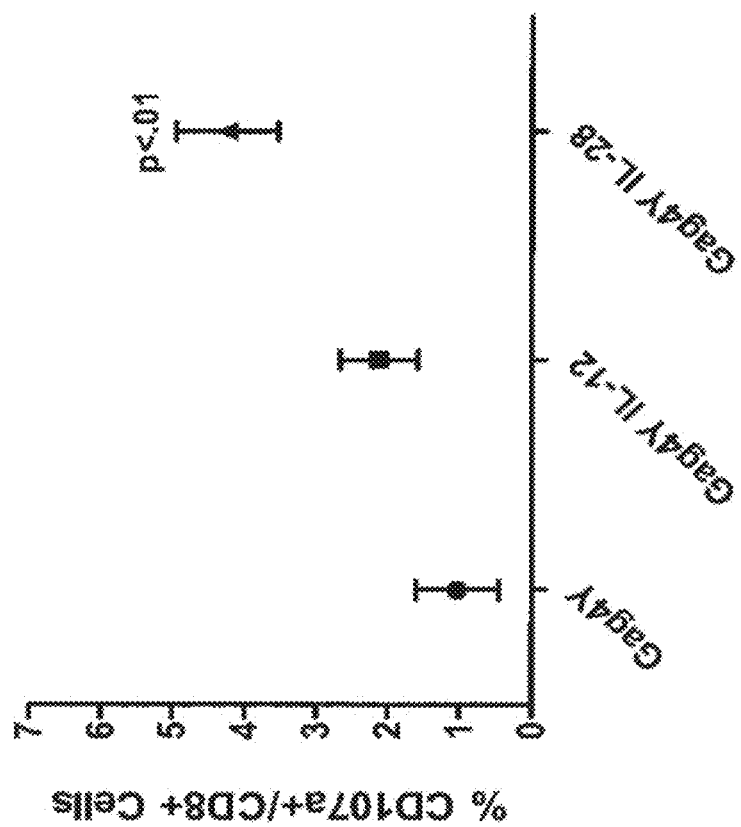
Figure 10C:
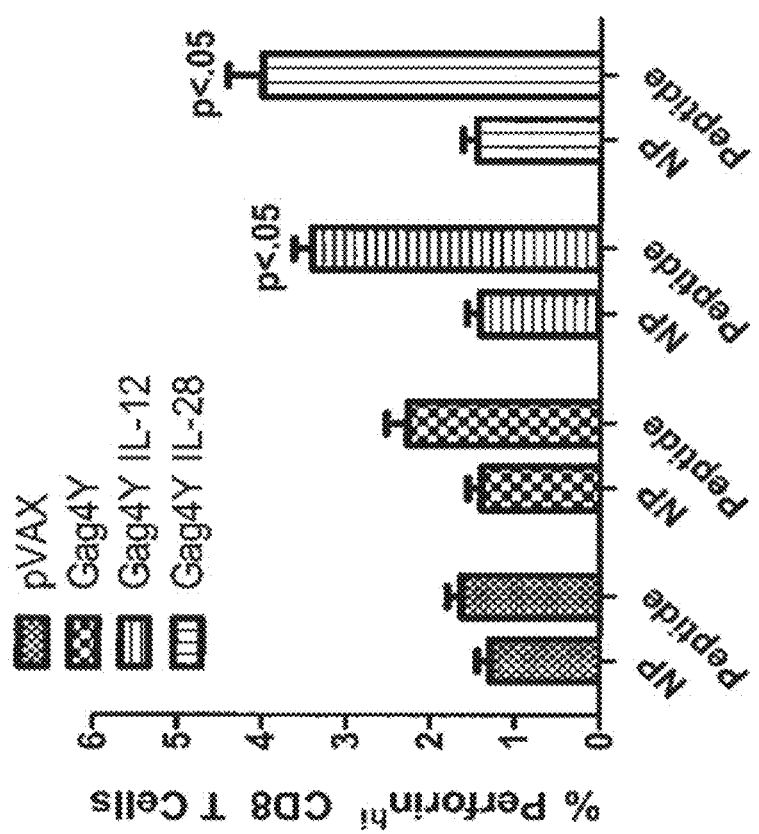

IL-28B Significantly Increases HIV Gag Specific CD8+ T Cell Perforin Induction and Degranulation Upon determining that IL-28B was having a significant impact on the percentage of splenic CD8+ T cells after vaccination, we decided to perform further analysis on this cellular subset. It has previously been shown that IL-12 may influence the granularity of CD8+ T cells[19]. As our previous experiments suggested that IL-28B was having a strong influence on cellular immunity (via IFNγ release) that was equal to or greater than IL-12 (FIG. 7A), we asked whether or not IL-28B could influence cell granularity in the same fashion as IL-12. Therefore, we designed experiments to measure the antigen-specific induction of perforin in CD8+ T cells isolated from the spleens of each group of mice. In order to determine the amount of antigen-specific perforin upregulation, we incubated isolated splenocytes with a media control or with a set of overlapping HIV Gag Clack C peptides for 6 hours, followed by extra- and intracellular staining for cellular markers and perforin, followed by analysis via flow cytometry (FIG. 10B). In order to prevent cytolytic degranulation, EGTA and $Mg^{+2}$ were added to cultures as described in Methods[17]. The results of this stimulation are presented in FIG. 10C. CD8+ T cells in splenocytes from all groups incubated with media alone showed roughly equivalent amounts of perforin, suggesting that vaccination, with or without adjuvants, had no significant affect on basal CD8+ T cell granularity in this system. Stimulation of splenocytes with overlapping HIV Gag peptides showed different results. CD8+ T cells in splenocytes from mice immunized with the HIV Gag4Y construct alone showed a modest increase in the percentage of cells falling into the Perforin$^{hi}$ gate (FIG. 10B) when compared to control mice. However, CD8+ T cells taken from mice that had received IL-12 or IL-28B both showed increases in Perforin$^{hi}$ cell percentages that were clearly higher than those taken from mice that received the Gag 4Y construct alone (FIG. 10C). This result is consistent with previous reports that IL-12 may increase the perforin content of lymphocytes[22] and is the first time this affect of has been reported for IL-28B.

With the knowledge that IL-28B could influence the perforin content of CD8+ T cells, we examined if this cytokine adjuvant could be affecting antigen-specific degranulation as well. To test this, we incubated cells in the same fashion as we did to measure perforin induction, save for the fact that no EGTA or $Mg^{+2}$ were added to cultures, and an antibody to CD107a, which is a marker for degranulation[23], was instead added at the time of peptide stimulation as an enhanced stain. Cells were again subjected to staining for cellular markers, followed by analysis via flow cytometry. We observed that CD8+ T cells from mice that had received the Gag 4Y construct alone showed a low level of Gag-specific degranulation (FIG. 10C). CD8+ T cells from mice that received IL-12 in combination with the HIV Gag 4Y construct showed a modest increase in antigen-specific degranulation when compared with mice that received the Gag construct alone, but this difference did not reach statistical significance. However, CD8+ T cells from mice that received the IL-28B plasmid as an adjuvant in vaccination showed a significant increase in HIV Gag-specific degranulation when compared with T cells taken from mice that did not receive adjuvant (FIG. 10C). The results show that IL-28B causes a major and statistically significant increase in CD8+ T cell degranulation when used as an adjuvant in DNA vaccination.

IL-28B Protects from a Lethal Influenza Challenge In Vivo

Figure 11A:
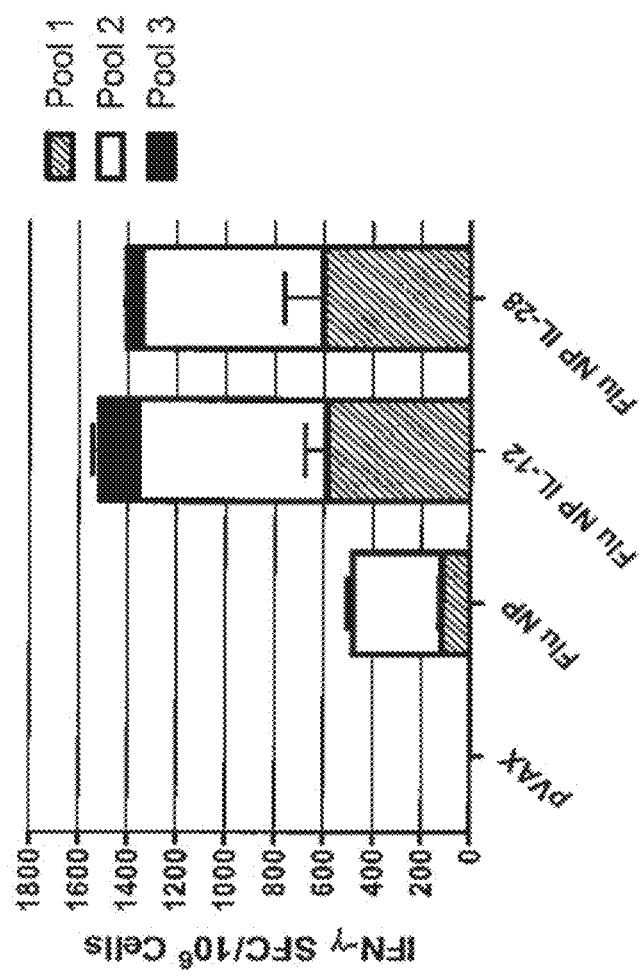
FIGS. 11A, 11B and 11C show protection from death in a lethal Influenza challenge.
Figure 11B:
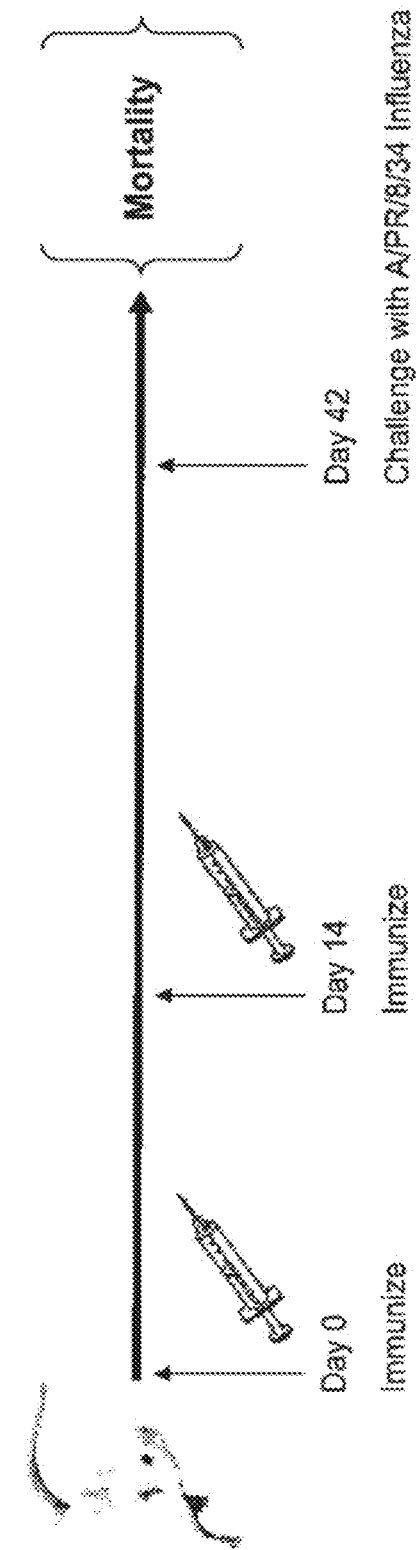
Figure 11C:
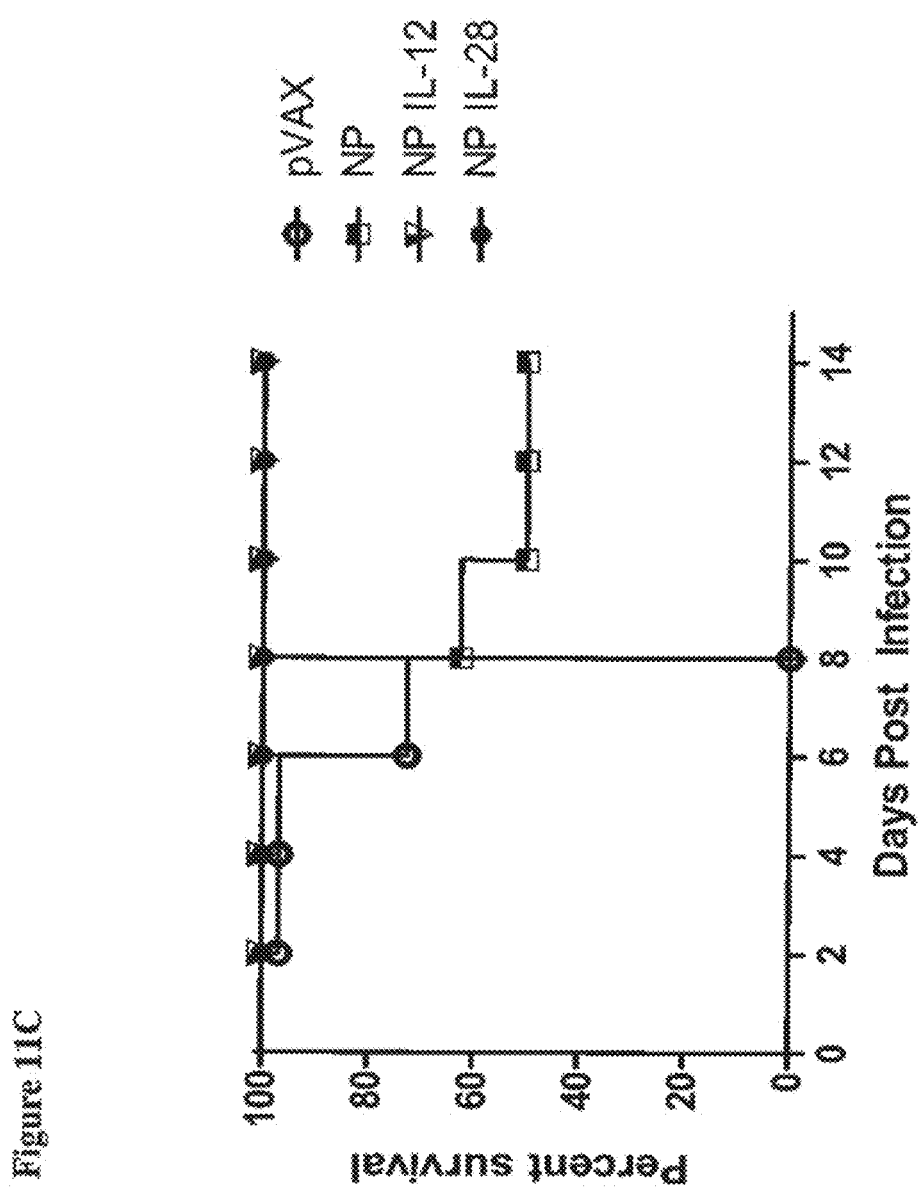

Since our assays for cellular immune responses suggested that IL-28B had the potential to act as a strong adjuvant for Th1 biased cellular immunity, we decided to test the ability of this cytokine to protect against a lethal viral challenge in vivo. In order to accomplish this, we immunized 4 additional sets of mice (n=8 mice per group) in the same fashion as above, followed by electroporation. Control mice received 10 µg of empty pVAX vector, while the other groups of mice received 10 µg of a plasmid encoding the influenza nucleoprotein (NP) alone or in addition to IL-12 or IL-28B. The nucleoprotein of influenza is an internal structural protein, and not exposed on the outside of the virion. Thus, immunity to influenza infection that is targeted against the NP protein is cellular, as apposed to humoral immunity[16]. Analysis of cellular immunity of vaccinated mice via IFNγ ELISpot showed that the IL-12 and IL-28B adjuvants induced increased responses to the Influenza NP antigen in much the same way it augmented responses to the HIV Gag4Y construct (FIG. 11A). After a 4 week rest period following immunization (FIG. 11B), all groups of mice were challenged intranasally with 10 LD50 of an H1N1 influenza strain: A/Puerto Rico/8/34 (A/PR/8/34). The mice were monitored over the course of the next 14 days for mortality associated with viral infection. Results of this experiment show that challenge of control mice resulted in 100% mortality by Day 8 post infection (FIG. 11C). Mice that received 10 µg of the NP construct showed 50% mortality over the following 14 days, suggesting that the NP construct alone was not completely sufficient to induce protection. IL-12, when used as an adjuvant in challenge studies, has been shown in the past to be able to induce significant protection against mortality associated with viral infections[13,14]. This is also the case in the current study, as exhibited by the fact that mice that received IL-12 as an adjuvant to NP showed 100% protection from death as a result of infection. Additionally, in agreement with our previous assays suggesting that IL-28B could induce potent cellular immune responses, mice who received IL-28B as an adjuvant to the NP construct also showed 100% survival after viral challenge. The results of this experiment show that IL-28B, when used as an adjuvant during DNA vaccination, may induce 100% protection from mortality associated with viral infection in vivo.

Discussion

The study presented here shows that plasmid encoded IL-28B may have potent affects on antigen-specific immune responses when used as an adjuvant in DNA vaccination. IL-28B was able to augment antigen-specific immune response to a multi-clade HIV Gag antigen in a Th1-biased fashion, which was evidenced by greatly enhanced IFNγ release during antigen-specific ELISpots as well as increased Gag-specific IgG2a levels detected in the sera of vaccinated mice. Additionally, this is the first report to describe the ability of IL-28B to reduce splenic Treg populations after DNA vaccination, a great potential benefit of this cytokine. IL-28B was also shown here to be able to expand the splenic CD8+ T cell population, and that these cells showed increased perforin induction and degranulation in response to cognate antigen. The fact that IL-28B was able to augment protection of mice in a lethal viral challenge model makes a strong case for continued testing of this cytokine as an adjuvant in vaccination.

The impact of IL-28B was measured against IL-12 due to the fact that IL-12 is known to be a highly potent cytokine that is used often as an adjuvant in vaccination studies[9-13]. Analysis of this comparison shows IL-28B to be at least as potent as IL-12 in some assays, if not better. Moreover, IL-28B affords additional benefits for vaccination that IL-12 does not, including increased antigen-specific antibody titers and an increased splenic CD8+ T cell population that is capable of higher degrees of antigen-specific cytolytic degranulation. The affects of IL-28B and IL-12 on Treg populations was dramatically different. This is the first study to analyze the induction of Tregs in response to IL-12 in DNA vaccination and to report that this adjuvant may increase this cell population. While the impact of this finding is not as yet clear, this result may support that IL-28B could be superior in specific situations where cellular immunity is paramount. The specific mechanism by which mice that received IL-12 had larger Treg populations remains unclear, although a recent report has highlighted the importance of the IL-12 receptor for the generation of Tregs in vivo[24], suggesting a possible link between this cytokine and the induction and expansion of the Treg population. The ability of IL-28B to reduce Treg numbers seems more likely to be a targeted mechanism, as it is able to increase some subsets of T cells (CD8) while reducing others (Treg). It is possible that this, too, is mediated through the IL-28 receptor, although additional studies into specific mechanisms are needed.

Results presented here include constitute a significant analysis of the function of IL-28B in vivo and contribute to the beginning of our understanding of how IL-28B affects immune responses. The data suggests that IL-28B may be a regulator of the adaptive immune response in addition to its IFN-like functions, and this affect seems to focus largely on the number and function of CD8+ T cells. The fact that IL-28B induces an antiviral state in addition to being able to shape antigen specific-immune responses suggests that it is has the unique ability to bridge the gap between innate and adaptive immunity. Furthermore IL-28B may have a unique role in immune therapy approaches over IL-12 in specific adjuvant settings. In particular as an adjuvant in tumor immunity where tolerance is particularly an issue, IL-28B may be very useful. Further studies are needed in order to properly verify this.

REFERENCES

1. Greenland J R, Letvin N L. Chemical adjuvants for plasmid DNA vaccines. Vaccine. 2007; 25:3731-3741.

2. Hokey D A, Weiner D B. DNA vaccines for HIV: challenges and opportunities. Springer Semin Immunopathol. 2006; 28:267-279.

3. Schoenly K A, Weiner D B. Human immunodeficiency virus type 1 vaccine development: recent advances in the cytotoxic T-lymphocyte platform "spotty business". J Virol. 2008; 82:3166-3180.

4. Ank N, West H, Paludan S R. IFN-lambda: novel antiviral cytokines. J Interferon Cytokine Res. 2006; 26:373-379.

5. Mennechet F J, Uze G. Interferon-lambda-treated dendritic cells specifically induce proliferation of FOXP3-expressing suppressor T cells. Blood. 2006; 107:4417-4423.

6. Sheppard P, Kindsvogel W, Xu W, et al. IL-28, IL-29 and their class II cytokine receptor IL-28R. Nat Immunol. 2003; 4:63-68.

7. Uze G, Monneron D. IL-28 and IL-29: newcomers to the interferon family. Biochimie. 2007; 89:729-734.

8. Siebler J, Wirtz S, Weigmann B, et al. IL-28A is a key regulator of T-cell-mediated liver injury via the T-box transcription factor T-bet. Gastroenterology. 2007; 132:358-371.

9. Boyer J D, Robinson T M, Kutzler M A, et al. SIV DNA vaccine co-administered with IL-12 expression plasmid enhances CD8 SIV cellular immune responses in cynomolgus macaques. J Med Primatol. 2005; 34:262-270.

10. Chong S Y, Egan M A, Kutzler M A, et al. Comparative ability of plasmid IL-12 and IL-15 to enhance cellular and humoral immune responses elicited by a SIVgag plasmid DNA vaccine and alter disease progression following SHIV(89.6P) challenge in rhesus macaques. Vaccine. 2007; 25:4967-4982.

11. Kim J J, Maguire H C, Jr., Nottingham L K, et al. Coadministration of IL-12 or IL-10 expression cassettes drives immune responses toward a Th1 phenotype. J Interferon Cytokine Res. 1998; 18:537-547.

12. Morrow M P, Weiner D B. Cytokines as adjuvants for improving anti-HIV responses. AIDS. 2008; 22:333-338.

13. Schadeck E B, Sidhu M, Egan M A, et al. A dose sparing effect by plasmid encoded IL-12 adjuvant on a SIVgag-plasmid DNA vaccine in rhesus macaques. Vaccine. 2006; 24:4677-4687.

14. Sin J I, Kim J J, Arnold R L, et al. IL-12 gene as a DNA vaccine adjuvant in a herpes mouse model: IL-12 enhances Th1-type CD4+ T cell-mediated protective immunity against herpes simplex virus-2 challenge. J Immunol. 1999; 162:2912-2921.

15. Hirao L A, Wu L, Khan A S, Satishchandran A, Draghia-Akli R, Weiner D B. Intradermal/subcutaneous immunization by electroporation improves plasmid vaccine delivery and potency in pigs and rhesus macaques. Vaccine. 2008; 26:440-448.

16. Laddy D J, Yan J, Kutzler M, et al. Heterosubtypic protection against pathogenic human and avian influenza viruses via in vivo electroporation of synthetic consensus DNA antigens. PLoS ONE. 2008; 3:e2517.

17. Wilson J L, Heffler L C, Charo J, Scheynius A, Bejarano M T, Ljunggren H G. Targeting of human dendritic cells by autologous NK cells. J Immunol. 1999; 163:6365-6370.

18. DeKruyff R H, Rizzo L V, Umetsu D T. Induction of immunoglobulin synthesis by CD4+ T cell clones. Semin Immunol. 1993; 5:421-430.

19. McFarland E J, Harding P A, MaWhinney S, Schooley R T, Kuritzkes D R. In vitro effects of IL-12 on HIV-1-specific CTL lines from HIV-1-infected children. J Immunol. 1998; 161:513-519.

20. Moore A C, Gallimore A, Draper S J, Watkins K R, Gilbert S C, Hill A V. Anti-CD25 antibody enhancement of vaccine-induced immunogenicity: increased durable cellular immunity with reduced immunodominance. J Immunol. 2005; 175:7264-7273.

21. Tang Q, Bluestone J A. The Foxp3+ regulatory T cell: a jack of all trades, master of regulation. Nat Immunol. 2008; 9:239-244.

22. Rubio V, Stuge T B, Singh N, et al. Ex vivo identification, isolation and analysis of tumor-cytolytic T cells. Nat Med. 2003; 9:1377-1382.

23. Belyakov I M, Derby M A, Ahlers J D, et al. Mucosal immunization with HIV-1 peptide vaccine induces mucosal and systemic cytotoxic T lymphocytes and protective immunity in mice against intrarectal recombinant HIV-vaccinia challenge. Proc Natl Acad Sci USA. 1998; 95:1709-1714.

24. Zhao Z, Yu S, Fitzgerald D C, et al. IL-12Rbeta2 promotes the development of CD4+CD25+ regulatory T cells. J Immunol. 2008; 181:3870-3876.

The invention claimed is:

1. An immunogenic pharmaceutical composition comprising:
   an isolated nucleic acid molecule that encodes an immunogen,
      wherein the immunogen is a viral protein, and wherein the nucleic acid molecule further comprises a nucleotide sequence that encodes an IgE signal peptide; and
   an isolated nucleic acid molecule that encodes IL-28 or functional fragments thereof.

2. The immunogenic pharmaceutical composition of claim 1, wherein the nucleic acid molecules are plasmids.

3. The immunogenic pharmaceutical composition of claim 1, wherein the viral protein is from a virus selected from the group consisting of influenza virus, human immunodeficiency virus, hepatitis C virus, West Nile Virus, and hepatitis B virus.

4. The immunogenic pharmaceutical composition of claim 3, wherein the viral protein is from an influenza virus.

5. An immunogenic pharmaceutical composition comprising an isolated nucleic acid molecule comprising a nucleotide sequence that encodes an immunogen; a nucleotide sequence that encodes an IgE signal peptide; and a nucleotide sequence that encodes IL-28 or a functional fragment thereof,
   wherein the immunogen is a viral protein.

6. The immunogenic pharmaceutical composition of claim 5, wherein the nucleic acid molecule is a plasmid.

7. The immunogenic pharmaceutical composition of claim 5, wherein the viral protein is from a virus selected from the group consisting of influenza virus, human immunodeficiency virus, hepatitis C virus, West Nile Virus, and hepatitis B virus.

8. The immunogenic pharmaceutical composition of claim 7, wherein the viral protein is from an influenza virus.

9. An injectable immunogenic pharmaceutical composition comprising the immunogenic pharmaceutical composition of claim 1.

10. A method of inducing an immune response in an individual against an immunogen comprising administering to said individual an immunogenic pharmaceutical composition of claim 1.

11. A method of inducing an immune response in an individual against an immunogen comprising administering to said individual an immunogenic pharmaceutical composition of claim 5.

12. A recombinant vaccine comprising a nucleotide sequence that encodes an immunogen operably linked to regulatory elements, a nucleotide sequence that encodes an IgE signal peptide, and a nucleotide sequence that encodes IL-28 or a functional fragment thereof,
   wherein the immunogen is a viral protein.

13. The recombinant vaccine of claim 12, wherein the viral protein is from a virus selected from the group consisting of influenza virus, human immunodeficiency virus, hepatitis C virus, West Nile Virus, and hepatitis B virus.

14. The recombinant vaccine of claim 13, wherein the viral protein is from an influenza virus.

15. The recombinant vaccine of claim 14, wherein the recombinant vaccine is a recombinant vaccinia vaccine.

16. A method of inducing an immune response in an individual against an immunogen comprising administering to said individual a recombinant vaccine of claim 12.

* * * * *